US008993716B2

(12) United States Patent
Serraïma et al.

(10) Patent No.: US 8,993,716 B2
(45) Date of Patent: Mar. 31, 2015

(54) PEPTIDES USED IN THE TREATMENT AND/OR CARE OF THE SKIN, MUCOUS MEMBRANES AND/OR HAIR AND ITS USE IN COSMETIC OR PHARMACEUTICAL COMPOSITIONS

(75) Inventors: Cristina Carreño Serraïma, Barcelona (ES); Wim Van Den Nest, Vilanova I la Geltru (ES); Ana Sempere Bonete, Elche-Alicante (ES); Antonio Ferrer Montiel, Alicante (ES); Nuria Almiñana Domenech, Barcelona (ES); Juan Cebrián Puche, Barcelona (ES)

(73) Assignees: Lipotec, S.A., Gava Barcelona (ES); BCN Peptides, S.A., Barcelona (ES)

( * ) Notice: Subject to any disclaimer, the term of this patent is extended or adjusted under 35 U.S.C. 154(b) by 179 days.

(21) Appl. No.: 13/502,274

(22) PCT Filed: Oct. 22, 2010

(86) PCT No.: PCT/EP2010/006454
§ 371 (c)(1),
(2), (4) Date: Jun. 26, 2012

(87) PCT Pub. No.: WO2011/047868
PCT Pub. Date: Apr. 28, 2011

(65) Prior Publication Data
US 2013/0101662 A1 Apr. 25, 2013

Related U.S. Application Data

(60) Provisional application No. 61/254,340, filed on Oct. 23, 2009.

(30) Foreign Application Priority Data

Oct. 23, 2009 (ES) .................................. 200930896

(51) Int. Cl.
| | | |
|---|---|---|
| A61K 38/00 | (2006.01) | |
| C07K 2/00 | (2006.01) | |
| C07K 4/00 | (2006.01) | |
| C07K 5/00 | (2006.01) | |
| C07K 7/00 | (2006.01) | |
| C07K 14/00 | (2006.01) | |
| A61K 8/64 | (2006.01) | |
| C07K 5/117 | (2006.01) | |
| A61Q 19/00 | (2006.01) | |
| C07K 5/10 | (2006.01) | |
| C07K 7/06 | (2006.01) | |

(52) U.S. Cl.
CPC . *A61K 8/64* (2013.01); *A61K 38/00* (2013.01); *C07K 5/1024* (2013.01); *A61Q 19/00* (2013.01); *C07K 5/10* (2013.01); *C07K 7/06* (2013.01)
USPC ........................................................ 530/300

(58) Field of Classification Search
None
See application file for complete search history.

(56) References Cited

U.S. PATENT DOCUMENTS

| 4,774,231 | A | 9/1988 | Petitou et al. |
|---|---|---|---|
| 4,975,441 | A | 12/1990 | Gibson |
| 5,015,470 | A | 5/1991 | Gibson |
| 5,081,151 | A | 1/1992 | Davis et al. |
| 5,124,354 | A | 6/1992 | Green |
| 5,348,945 | A | 9/1994 | Berberian et al. |
| 5,942,494 | A | 8/1999 | Ginsberg et al. |
| 7,128,914 | B2 | 10/2006 | Leclerc et al. |
| 2002/0001629 | A1 | 1/2002 | Voellmy |
| 2004/0228816 | A1 | 11/2004 | Nizard et al. |
| 2006/0088560 | A1 | 4/2006 | Charrier et al. |
| 2006/0134048 | A1 | 6/2006 | Shander et al. |
| 2008/0070268 | A1 | 3/2008 | Anderson et al. |
| 2010/0119533 | A1 | 5/2010 | Clancy et al. |

FOREIGN PATENT DOCUMENTS

| EP | 0064012 | 11/1982 |
|---|---|---|
| EP | 0211610 | 2/1987 |
| EP | 0277428 | 8/1988 |
| EP | 0334586 | 9/1989 |
| EP | 0375388 | 6/1990 |
| EP | 0403238 | 12/1990 |
| FR | 2834887 | 7/2003 |
| MX | 2007007622 | 8/2007 |
| WO | 0124810 | 4/2001 |

(Continued)

OTHER PUBLICATIONS

Leshin L, MD ( * > Leshin L, MD, < Dermatologic Disorders in Down Syndrome [online], [retrieved on May 29, 2013]. Retrieved from the Internet <URL: * > http://www.ds-health.com/derm.htm < >).*

Better Health Channel of the Australian government < Hair Loss [online], [retrieved on May 29, 2013]. Retrieved from the Internet <URL: * > http://betterhealthchannel.vic.gov.au/bhcv2/bhcarticles.nsf/pages/Hair_loss?Open< >.*

University of Pennsylvania Health System (< Types of Hair Loss [online], [retrieved on May 29, 2013]. Retrieved from the Internet <URL: * > http://www.pennmedicine.org/hairtransplant/types.html< >).*

(Continued)

*Primary Examiner* — Marcela M Cordero Garcia
*Assistant Examiner* — Sergio Coffa
(74) *Attorney, Agent, or Firm* — Fay Sharpe LLP

(57) ABSTRACT

Peptides of general formula (I): $R_1—W_n—X_m-AA_1-AA_2-AA_3-AA_4-Y_p—Z_q—R_2$ (I) its stereoisomers, mixtures thereof and/or their cosmetically or pharmaceutically acceptable salts, a preparation process, cosmetic or pharmaceutical compositions which contain them and their use in the treatment and/or care of the skin, mucous membranes and/or hair and the treatment and/or care of those conditions, disorders and/or diseases which are improved or prevented by Hsp stimulation.

17 Claims, No Drawings

(56) References Cited

FOREIGN PATENT DOCUMENTS

| WO | 2008109833 | | 9/2008 |
| WO | WO 2008/109833 | * | 9/2008 |

OTHER PUBLICATIONS

The Mayo Clinic (< Epidermolysis bullosa [online], [retrieved on May 29, 2013]. Retrieved from the Internet <URL: * > http://www.mayoclinic.com/health/epidermolysis-bullosa/DS01015< >).*
The Merck manual (<Alopecia [online], [retrieved on May 29, 2013]. Retrieved from the Internet <URL: * > http://www.merckmanuals.com/professional/dermatologic_disorders/hair_disorders/alopecia.html?qt=alopecia&alt=sh< >).*
International Search Report for PCT/EP2010/006454, Completed by the European Patent Office on Mar. 3, 2011, 4 Pages.
Joint Commussion on Biochemical Nomenclature Eur. J. Biochem. 1984, vol. 138, p. 9-37, "Nomenclature and Symbolism for Amino Acids and Peptides."
Roberts et al. The peptides 1983, vol. 5, Chapter 6, 55 Pages, "Unusual Amino Acids in Peptide Synthesis."
Berge et al. "Review Article, Pharmaceutical Salts." Journal of Pharmaceutical Sciences Jan. 1977, vol. 66, No. 1, p. 1-19.
Stewart et al. Solid Phase Peptide Synthesis Second Edition 1984, 20 Pages, "The Chemistry of Solid Phase Peptide Synthesis."
Bodanszky et al. The Practice of Peptide Synthesis second edition 1984, "Activation and Coupling", All together 54 Pages.
Lloyd-Williams et al. "Chemical Approaches to the Synthesis of Peptides and Proteins." Chemical Approaches to the Synthesis of Peptides and Proteins 1997, 78 Pages.
Kullmann. "Proteases as Catalysts for Enzymic Syntheses of Opioid Peptides* ", The Journal of Biological Chemistry Issue of Sep. 10, 1980, vol. 255, No. 17, p. 8234-8238.
Lloyd-Williams et al. "Tetragedron Report No. 347: Convergent Solid-Phase Peptide Synthesis", Tetrahedron 1993, vol. 49, No. 48, p. 11065-11133.
Smith et al. 1999, 5th edition, 111 Pages, "March's Advanced Organic Chemistry Reactions, Mechanisms, and Structure."
Greene et al. "Protective Groups in Organic Synthesis." Protective Groups in Organic Synthesis 1999, Third Edition, 20 Pages.
Atherton et al. "Solid phase peptide synthesis." Oxford University Press 1989, 17 Pages.
Matsueda et al. "A p-Methylbenzhydrylamine Resin for Improved Solid-Phase Synthesis of Peptide Amides." Peptides 1981, vol. 2, p. 45-50.
Barlos et al. "Veresterung Von Partiell Geschutzten Peptid-Fragmenten Mit Harzen. Einsatz Von @-Chlortritylchlorid Zur Synthese Von Leu—Gastrin I", Tetrahedron Letters 1989, vol. 30, No. 30, p. 3947-3950.
Barlos et al. "Darstellung Geschutzter Peptide-Fragmente Unter Einsatz Substituierter Triphenylmethyl-Harze", Tetrahedron Letters 1989, vol. 30, No. 30, p. 3943-3946.
Albericio et al. "Preparation and Application of the 5-(4-(9-Flyorenylmethyloxycarbonyl)Aminomethyl-3,5-Dimethoxyphenoxy)—Valeric Acid (PAL) Handle for the Solid-Phase Synthesis of C-Terminal Peptide Amides Under Mild Conditions 1-3", J. Org. Chem. 1990, vol. 55, p. 3730-3743.
Rink, Tetrahedron Letters 1987, vol. 28, No. 33, p. 3787-3790, "Solid-Phase Synthesis of Protected Peptide Fragements Using a Trialkoxy-Diphenyl-Methylester Resin."
Wang. "p-Alkoxybenzyl Alcohol Resin and p-Alkoxybenzyloxycarbonylhydrazide Resin for Solid Phase Syntheis of Protected Peptide Fragements." Journal of the American Chemical Society Feb. 21, 1973, vol. 95, p. 1328-1333.
Dweck. R.G. Harry Cosmeticology 8th edition, 2000, 27 Pages, "Botanicals in Cosmetics & Toiletries."
Remington, 21st edition, 2005, "The Science and Practice of Pharmacy." 60 Pages.
Schabb. Happi, May 1986, p. 84-86, "Impregnating Fabrics With Microcapsules."
Nelson. "Application of Microencapsulation in Textiles", International Journal of Pharmaceutics 2002, vol. 242, p. 55-62.
Hipler et al. Biofunctional Textiles and the Skin 2006, vol. 33, 10 Pages, "Current Problems in Dermatology."
Malcolm et al. "Controlled Release of Model Antibacterial Drug From a Novel Self-Lubricating Silicone Biomaterial", Journal of Controlled Release 2004, vol. 97, p. 313-320.
Fauli. Treated Galenic Pharmacy 1993, "Pharmaceutical Technology", English translation of first paragraph, 8 Pages.
Gottschalck et al. International Cosmetic Ingredient Dictionary and Handbook, 12th edition 2008, vol. 3, 14 Pages, "Biological Polymers and their Derivatives (Including salts, excluding gums, hydrophilic colloids and derivatives)."
Kaiser et al. "Color Test for Detection of Free Terminal Amino Groups in the Solid-Phase Synthesis of Peptides." Anal Biochem 1970, vol. 34, p. 595-398.
Christensen, Acta Chemica Scandinavica B 1979, vol. 33, p. 763-766, "A Qualitative Test for Monitoring Coupling Completeness in Solid Phase Peptide Synthesis Using Chloranil."
Hayes et al. The Journal of Cell Biology Feb. 1996, vol. 132, p. 255-258, "Roles of Molecular Chaperones in Protein Degradation."
Bases, Cell Stress & Chaperones 2006, vol. 11, No. 3, p. 240-249, "Heat shock protein 70 enhanced deoxyribonucleic acid base excision repair in human leukemic cells after ionizing radiation."
Niu et al. Cell Stress & Chaperones 2006, vol. 11, No. 2, p. 162-169, "Overexpressed heat shock protein 70 protects cells against DNA damage caused by ultraviolet C in a dose-dependent manner."
Nagelidis et al. Eur. J. Biochem. 1991, vol. 199, p. 35-39, "Constitutive expression of heat-shock protein 70 in mammalian cells confers thermoresistance."
Li et al. PNAS USA Mar. 1991, vol. 88, p. 1681-1685, "Thermal response of rat fibroblasts stably transfected with the human 70-kDa heat shock protein-encoding gene."
Trautinger et al. The Journal of Investigative Dermatology Aug. 1995, vol. 105, No. 2, p. 160-162, "72-kD Heat Shock Protein Is a Mediator of Resistance to Ultraviolet B Light."
Simon et al. J. Clin. Invest. Mar. 1995, vol. 95, p. 926-933, "Heat Shock Protein 70 Overexpression Affects the Response to Ultraviolet Light in Murine Fibroblasts."
Gu et al. Molecular Bioloty of the Cell Mar. 2005, vol. 16, p. 1427-1438, "Defining the Properties of the Nonhelical Tail Domain in Type II Keratin 5: Insight from a Bullous Disease-causing Mutation."
Laplante et al. Journal of Histochemistry & Cytochemistry 1998, vol. 46, p. 1291-1301, "Expression of Heat Shock Proteins in Mouse Skin During Wound Healing."
Trautinger et al. Letters to the Editor Sep. 1996, vol. 107, No. 3, p. 442-443, "Increased Expression of the 72-kDa Heat Shock Protein and Reduced Sunburn Cell Formation in Human Skin After Local Hyperthermia."
Lionakis et al. Infection and Immunity Nov. 2005, vol. 73, No. 11, p. 7747-7758, "Development of a Ligand-Directed Approach to Study the Pathogenesis of Invasive Aspergillosis."
Atalay et al. Current Protein and Peptide Science 2009, vol. 10, p. 85-95, "Heat Shock Proteins in Diabetes and Wound Healing."
Anathan et al. Science 1986, vol. 232, p. 522-524, "Abnormal Proteins Serve as Eukaryotic Stress Signals and Trigger the Activation of Heat Shock Genes."
Bitar et al. Surgery Feb. 20, 1999, vol. 125, No. 6, p. 594-601, "Heat-shock protein 72-72 and impaired wound healing in diabetic and hypercortisolemic states."
Kovalchin et al. Wound Rep Reg 2006, vol. 14, p. 129-137, "In vivo delivery of heat shock protein 70 accelerates wound healing by up-regulating macrophage-mediated phagocytosis."
Gething et al. Nature Jan. 2, 1992, vol. 355, p. 33-45, "Protein folding in the cell."
Lis et al. Cell Jul. 16, 1993, vol. 74, p. 1-4, "Proetin Traffic on the Heat Shock Promoter: Parking, Stalling and Trucking Along."
Daniels et al. Molecular Pharmacology 1995, vol. 48, p. 425-432, "Structure-Activity Relationship of Novel Pentapeptide Neuropeptide Y Receptor Antagonists Is Consistent with a Noncontinuous Epitope for Ligand-Receptor Binding."

(56) References Cited

OTHER PUBLICATIONS

Lindquist, Ann. Rev. Biochem. 1986, vol. 55, p. 1151-1191, "The Heat-Shock Response."

Kampinga et al. Experimental Cell Research 1995, vol. 219, p. 536-546, "Thermal Protein Denaturation and Protein Aggregation in Cells Made Thermotolerant by Various Chemicals: Role of Heat Shock Proteins."

Subjeck et al. British Journal of Radiology Aug. 1982, vol. 55, p. 579-584, "Heat shock proteins and thermotolerance; a comparison of induction kinetics."

McMurtry et al. Journal of Surgical Research 1999, vol. 86, p. 36-41, "Expresxsion of HSP70 in Healing Wounds of Diabetic and Nondiabetic Mice."

Verbeke et al. Cell Biology International 2001, vol. 25, No. 9, p. 845-857, "Heat Shock Response and Ageing: Mechanisms and Applications."

* cited by examiner

PEPTIDES USED IN THE TREATMENT AND/OR CARE OF THE SKIN, MUCOUS MEMBRANES AND/OR HAIR AND ITS USE IN COSMETIC OR PHARMACEUTICAL COMPOSITIONS

CROSS-REFERENCE TO RELATED APPLICATION

This application is the U.S. national phase of PCT Appln. No. PCT/EP2010/006454 filed on Oct. 22, 2010, which claims priority to ES Patent Application No. 200930896 filed on Oct. 23, 2009, and claims the benefit of U.S. Provisional Application No. 61/254,340 filed on Oct. 23, 2009 the disclosures of which are incorporated in their entirety by reference herein.

FIELD OF THE INVENTION

This invention relates to peptides capable of inducing the expression of heat shock proteins in the skin, mucous membranes and/or hair and to cosmetic or pharmaceutical compositions which contain these peptides used in the treatment and/or care of the skin, mucous membranes and/or hair, preferably for the treatment and/or care of those conditions, disorders and/or diseases of the skin, mucous membranes and/or hair which are improved or prevented by a stimulation of heat shock protein synthesis.

BACKGROUND OF THE INVENTION

Skin, mucous membranes and hair are constantly exposed to stressful factors, both of a chemical and physical nature. Solar radiation, the exposure to certain chemical agents or high temperatures can have harmful effects on the cells which make up the skin, accelerating its aging and making it look unhealthy. The mechanisms through which ultraviolet radiation (UV) exercises these effects includes the formation of reactive oxygen species, damage to the DNA, and the denaturation of proteins, among others.

Denaturation or change in the proteins' conformation can imply the exposure of hydrophobic residues at the protein surface, a situation in which the proteins are susceptible to forming aggregates, thus losing their functionality. This is dangerous for the integrity of the cell, and therefore it has specialized mechanisms to combat the aforementioned situations: all the live organisms have mechanisms to prevent the damage caused by accumulation of misfolded proteins [Ananthan J., Goldberg A. L. and Voellmy R. (1986) "*Abnormal proteins serve as eukaryotic stress signals and trigger the activation of heat shock genes*" Science 232:522-524].

It has been seen that the cells respond to a stressful situation by increasing synthesis of the so-called stress proteins. This response begins when the cell detects an accumulation of abnormally folded proteins, giving rise to an increase in the transcription of heat shock genes X is J. and Wu C. (1993) "*Protein traffic on the heat shock promoter: parking, stalling, and trucking along*" Cell 74:1-4]. The products of these genes are classified into two large groups, heat shock proteins and glucose regulated proteins. The term "heat shock protein" originates from the observation of an increase of these proteins' synthesis in cells incubated at an abnormally high temperature. These proteins' synthesis is also increased not just when the cells are subjected to an increase in temperature, but also in other stressful situations such as exposure to UV radiation, oxidative stress, osmotic shock, inflammation, hypoxia, exposure to pollutants such as heavy metals, lack of nourishment and lack of hydration [Lindquist S. (1986) "*The heat-shock response*" Annu. Rev. Biochem. 55:1151-1191].

Heat shock proteins are a family of proteins classified according to their molecular weight, the one that have been subject to more studies are 60 kDa and 70 kDa proteins, due to their constituent expression in all cells and their direct participation in several aspects of protein maturation. Hsp70 principally comprises two proteins: Hsp73, the form expressed constituently, and Hsp72, the inducible form, which is transcriptionally regulated by the heat shock factor protein 1 (HSF1). These proteins are also called molecular chaperones, due to their function of directing the folding of recently synthesized proteins from a globule-like conformation merged to a final compact structure, avoiding the appearance of conformations susceptible to forming aggregates and, therefore, ensuring their correct functionality. In normal conditions, Hsp70 is located in the nucleus and cytoplasm and interacts transitorily with the newborn proteins, it facilitates their folding and promotes their translocation through the Golgi complex and endoplasmic reticulum, in joint action with Hsp60. In stressful conditions, however, Hsp70 forms a complex with the unfolded proteins or erroneously folded proteins, to rescue them from degradation and irreversible damage, or the opposite, to increase the possibilities of a proteolytic attack in the event that it is impossible to protect them [Hayes S. A. and Dice J. F. (1996) "Roles of molecular chaperones in protein degradation" J. Cell. Biol. 132:255-258; Gething M. J. and Sambrook J. (1992) "*Protein folding in the cell*" Nature 355:33-45]. Neither Hsp70 or Hsp60 end up forming part of the final correctly folded protein, nor do they possess any specific information on the folding; they simply prevent inappropriate interactions from being established which may cause misfolding or lead to aggregations and, therefore, loss of functionality. The mechanism through which the protein adopts its definitive conformation is, however, unknown.

As well as the chaperone functions reestablishing the conformation of badly-folded proteins, the participation of Hsp70 has been described in processes of protection and repair of DNA in the case of damage caused to them by UV radiation or ionizing radiation [Bases R. (2006) "*Heat shock protein 70 enhanced deoxyribonucleic acid base excision repair in human leukemic cells after ionizing radiation*" Cell Stress Chaperones 11:240-249; Niu P., Liu L., Gong Z., Tan H., Wang F., Yuan J., Feng Y, Wei Q., Tanguay R. M. and Wu T. (2006) "*Overexpressed heat shock protein 70 protects cells against DNA damage caused by ultraviolet C in a dose-dependent manner*" Cell Stress & Chaperones 11:162-169].

The response to stress constitutes a universally conserved cell defense mechanism which is reflected in the so-called acquired thermotolerance, a phenomenon according to which cells that suffer a non-lethal thermal shock are capable, after a recovery period at normal growth temperature, of surviving a second thermal shock which would have been lethal the first time around [Subjeck J. R., Sciandra J. J. and Johnson R. J. (1982) "*Heat shock proteins and thermotolerance; a comparison of induction kinetics*" Br. J. Radiol. 55:579-584; Angelidis C. E., Lazaridis I. and Pagoulatos G. N. (1991) "*Constitutive expression of heat-shock protein 70 in mammalian cells confers thermoresistance*" Eur. J. Biochem. 199:35-39; Li G. C., Li L. G., Liu Y. K., Mak J. Y., Chen L. L. and Lee W. M. (1991) "*Thermal response of rat fibroblasts stably transfected with the human 70-kDa heat shock protein-encoding gene*" Proc. Natl. Acad. Sci. USA 88:1681-1685]. This acquired thermotolerance has been seen to be transitory, it usually lasts between 12 and 24 hours in growing cells, and depends on the changes induced by the shock of the initial temperature, such as levels of increase in the expression and accumulation of shock proteins. Within the Hsp family it has been verified that Hsp70 is responsible for induction of thermotolerance: specific inhibition both of the transcription as well as the synthesis of Hsp72 prevents the protecting effects induced by thermal treatment [Trautinger F., Kindås-Mügge I., Barlan B., Neuner P. and Knobler R. M. (1995) "*72-kD heat shock protein is a mediator of resistance to ultraviolet B light*" *J. Invest. Dermatol.* 105:160-162; Simon M. M., Reikerstorfer A., Schwarz A., Krone C., Luger T. A., Jäättelä M. and Schwarz T. (1995) "*Heat shock protein 70 overexpression affects the response to ultraviolet light in murine fibroblasts. Evidence for increased cell viability and suppression of cytokine release*" *J. Clin. Invest.* 95:926-33].

Subsequently it was verified that any agent or treatment capable of inducing a response to stress provides the cell with protection in the face of a subsequent exposure to a stress-causing agent, regardless of the origin of that stress [Kampinga H. H., Brunsting J. F., Stege G. J. J., Burgman P. W. J. J. and Konings A. W. T (1995) "*Thermal protein denaturation and protein aggregation in cells made thermotolerant by various chemicals: role of heat shock proteins*" *Exp. Cell Res.* 219:536-546]. Exogenous induction of the expression of shock proteins is, therefore, a plausible strategy to prevent damage to cell proteins and, therefore, maintain cell integrity.

Described in the literature are different diseases which are caused by abnormal protein folding, such as epidermolysis bullosa [Gu L. H. and Coulombe P. A. (2005) "*Defining the properties of the nonhelical tail domain in type II keratin 5: insight from a bullous disease-causing mutation*" *Mol Biol Cell.* 16:1427-1438], which is caused by the incorrect folding of keratin caused by mutations of some amino acids in its sequence. These diseases are subject to treatment with compounds which induce an increase in the levels of heat shock proteins.

In the same way, compounds which induce an increase in the expression of heat shock proteins are used in the treatment and/or care of wounds or as adjuvants in healing and/or re-epithelialization processes. It is known that wound healing and repair processes present an increase in the expression of heat shock proteins. Specifically, induction of the expression of Hsp in the case of cutaneous trauma is specific to the location of the keratinocytes in the skin; thus, Hsp70 sees its synthesis induced in epidermis keratinocytes [Laplante A. F., Moulin V., Auger F. A., Landry J., Li H., Morrow G., Tanguay R. M. and Germain L. (1998) "*Expression of heat shock proteins in mouse skin during wound healing*" *J. Histochem. Cytochem.* 46:1291-301]. It has also been observed that the external delivery of the Hsp70 protein accelerates wound healing [Kovalchin J. T., Wang R., Wagh M. S., Azoulay J., Sanders M. and Chandawarkar R. Y. (2006) "*In vivo delivery of heat shock protein 70 accelerates wound healing by up-regulating macrophage-mediated phagocytosis*" *Wound Repair Regen.* 14:129-137]. A decrease in the quantity of Hsp70 in the skin of diabetic patients with impaired wound healing and repair has also been described [Bitar M. S., Farook T., John B. and Francis I. M. (1999) "*Heat-shock protein 72/73 and impaired wound healing in diabetic and hypercortisolemic states*" *Surgery* 125:594-601; Atalay M., Oksala N., Lappalainen J., Laaksonen D. E., Sen C. K. and Roy S. (2009) "*Heat shock proteins in diabetes and wound healing*" *Curr. Protein Pept. Sci.* 10:85-95; McMurtry A. L., Cho K., Young L. J.-T., Nelson C. F. and Greenhalgh D. G. (1999) "*Expression of HSP70 in healing wounds of diabetic and nondiabetic mice*" *J. Surg. Res.* 86:36-41]. Thus, the induction of heat shock protein synthesis of is a valid strategy for the treatment and/or care of skin and/or mucous membrane wounds and, specifically, in the healing and re-epithelialization of skin and/or mucous membrane wounds which are a consequence of diabetes.

The participation of Hsp70 in the regulation of hair growth is also known in the prior art; specifically patent application MX 2007-007622 describes the application of compounds inhibiting synthesis of Hsp70 to reduce hair growth. The implication of Hsp70 in the regulation of hair growth suggests the use of compounds capable of stimulating Hsp synthesis for the treatment and/or prevention of alopecia in order to delay hair loss or induce hair growth and, specifically, for the treatment of alopecia caused by chemotherapy as a treatment for cancer as described in patent US 2002/0001629.

Abnormal protein folding also has an effect on the skin from an aesthetic point of view. Correct elastin and collagen protein folding is fundamental to maintain the flexibility of the skin and smooth and young looking skin. Young adults' skin is particularly well adapted to respond quickly and effectively to stressful situations since it is capable of synthesizing great quantities of Hsp to protect protein folding during synthesis. However, in people of an advance age the ability to maintain correct protein folding is reduced since there is a reduction in Hsp70 synthesis with age, which causes an accumulation of damaged proteins or poorly folded and poor regulation of cell death which make the skin look old [Verbeke P, Fonager J, Clark B F, Rattan S I. (2001) "*Heat shock response and ageing: mechanisms and applications*" *Cell Biol. Int.* 25:845-857]. The effect that abnormal protein folding has on the skin from an aesthetic point of view is worsened when the skin is exposed to UV radiation, and contributes to the aspect of photoaged skin. UV radiation is capable of irreversibly damaging cells, causing cell death. However, it has been demonstrated that the exposure to high temperatures has a certain protective effect on cells, reducing the amount of cell death induced by UVB [Trautinger F., Knobler R., Hönigsmann H., M. Mayr W. and Kindås-Mügge I. (1996) "*Increased expression of the 72-kD heat shock protein and reduced sunburn cell formation in human skin after local hyperthermia*" *J. Invest. Dermatol.* 107:442-443]. This exposure to high temperatures induces Hsp synthesis. These are responsible for the photoprotective effect on the harmful effects of UV radiation observed. Thus, heat shock protein synthesis induction is a valid strategy for the treatment and/or care of the skin and/or hair with the aim of reducing, delaying and/or preventing the signs of aging and/or photoaging.

Both the cosmetic and pharmaceutical sector have carried out different tests in the development of compounds capable of stimulating heat shock protein synthesis. The role played by the heat shock proteins in different conditions, disorders and diseases is widely known in the prior art, as can found, for example, in the periodical publication *Heat Shock Proteins in Biology and Medicine* (Research Signpost, India) or *Cell Stress and Chaperones* (Springer, Netherlands), among others.

It is known that some serine protease inhibitors are capable of stimulating the production of heat shock proteins, but their high toxicity prevents their use for therapeutic purposes. Because of this, the industry needs to find agents with these properties and which can also be used risk-free for the patient's or consumer's health.

Different natural extracts which stimulate Hsp synthesis are described in the prior art, such as rye seed extracts, extracts of *Opuntia ficus-indica*, extracts which contain mangiferin (US 2006/0088560) or those described in documents US 2004/0228816, U.S. Pat. No. 7,128,914 or FR 2834887 among others. The difficulties of obtaining extracts with a homogenous quality and known composition and purity make their industrial development difficult, particularly in the pharmaceutical sector. Different modified synthetic peptides are also described with aldehyde or α-ketoester functions which induce Hsp synthesis, such as those described in U.S. Pat. No. 5,942,494. However, the aldehyde function is chemically incompatible with a great quantity of ingredients commonly employed in topical application formulations, also showing problems of low stability in the formulations, which limits its use in the cosmetic or dermopharmaceutical sector.

The benefit of the action of heat shock proteins on the skin, mucous membranes and/or hair could also be obtained from direct application of these proteins to the skin; mucous membranes and/or hair. In this sense, U.S. Pat. No. 5,348,945 describes the exogenous application of protein Hsp70 as a method for reducing the mortality of a tissue subjected to stressful situations and, especially, to preserve tissues which are to be used in organ transplants. The topical application of proteins with a high molecular weight presents the difficulty of their low permeability through the skin and hair, thus making its development in the cosmetic or dermopharmaceutical sector difficult.

This is why despite the great number of existing compounds and/or extracts, there is still a need to identify new compounds stimulating heat shock protein synthesis which are more effective and selective than those known in the prior art.

DETAILED DESCRIPTION OF THE INVENTION

This invention provides a solution to the aforementioned problem. The applicant of this invention has surprisingly found that synthetic peptides whose sequence does not include aldehyde functionalizations are capable of stimulating Hsp70 protein synthesis and, therefore, are capable of protecting the skin, mucous membranes and/or hair against aggressions resulting from the exposure to stressful situations. These peptides are used in the treatment and/or care of the skin, mucous membranes and/or hair, preferably for the treatment and/or care of those conditions, disorders and/or diseases of the skin, mucous membranes and/or hair which are improved or prevented by heat shock protein stimulation.

DEFINITIONS

In order to facilitate the comprehension of this invention, the meanings of some terms and expressions as used in the context of the invention are included.

Within the context of this invention "skin" is understood to be the layers which comprise it from the outermost layer or stratum corneum to the lowermost layer or hypodermis, both inclusive. These layers are comprised by different types of cells such as keratinocytes, fibroblasts, melanocytes and/or adipocytes among others.

In the context of this invention, the term "skin" includes the scalp.

In the context of this invention "care of the skin, mucous membranes and/or hair" comprises the prevention of disorders and/or diseases of the skin, mucous membranes and/or hair.

In the context of this invention, the term "aging" refers to the changes experienced by the skin with age (chronoaging) or by exposure to the sun (photoaging) or to environmental agents such as tobacco smoke, extremely cold or windy weather, chemical pollutants or pollution, and includes all external visible and/or noticeable through touch, such as and not restricted to, the development of discontinuities on the skin such as wrinkles, fine lines, cracks, irregularities or roughness, increase in the size of pores, loss of elasticity, loss of firmness, loss of resilience, loss of the ability to recover from deformation, sagging of the skin such as sagging cheeks, appearance of bags under the eyes or appearance of a double chin among others, changes in skin color such as marks, redness, bags or the appearance of hyperpigmented areas such as age spots or freckles among others, abnormal differentiation, hyperkeratinization, elastosis, keratosis, hair loss, orange-peel skin, loss of collagen structuring and other histological changes to the stratum corneum, the dermis, the epidermis, the vascular system (for example the appearance of spider veins or telangiectasias) or to those tissues close to the skin among others. The term "photoaging" groups the set of processes due to the prolonged exposure of the skin to ultraviolet radiation that result in the premature aging of the skin, and presents the same physical characteristics as aging, such as and not excluding, flaccidity, sagging, changes in color or irregularities in pigmentation, abnormal and/or excessive keratinization.

In the context of this invention "photoprotection" is understood to be the ability of a compound or a formulation to prevent or delay the appearance of the symptoms of photoaging when this compound or formulation is applied before exposure to UV radiation.

In this description the abbreviations used for amino acids follow the IUPAC-IUB Joint Commission on Biochemical Nomenclature rules outlined in *Eur. J. Biochem.* (1984) 138: 9-37 and in *J. Biol. Chem.* (1989) 264:633-673.

Thus, for example, Asn represents $NH_2$—CH($CH_2CONH_2$)—COOH, Asn- represents $NH_2$—CH($CH_2CONH_2$)—CO—, -Asn represents —NH—CH($CH_2CONH_2$)—COOH and -Asn- represents —NH—CH($CH_2CONH_2$)—CO—. Therefore, the dash, which represents the peptide bond, eliminates the OH of the 1-carboxyl group of the amino acid (represented here in the non-ionized conventional form) when located at the right of the symbol, and eliminates the H of the 2-amino group of the amino acid when located at the left of the symbol; both modifications can be applied to the same symbol (see Table 1).

TABLE 1

Amino acid structures and their three letter nomenclature code.

| Symbol | Remainder |
|--------|-----------|
| -Arg- | 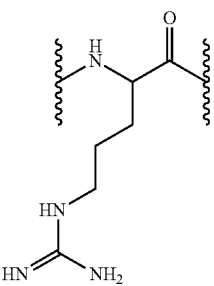 [SMILES: *NC(CCCNC(=N)N)C(*)=O] |

TABLE 1-continued

Amino acid structures and their three letter nomenclature code.

| Symbol | Remainder |
|---|---|
| -His- | 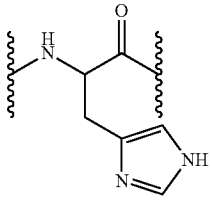 [SMILES: *NC(Cc1c[nH]cn1)C(*)=O] |
| -Asn- | 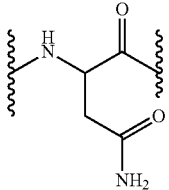 [SMILES: *NC(CC(N)=O)C(*)=O] |
| -Leu- | 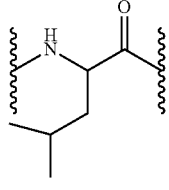 [SMILES: *NC(CC(C)C)C(*)=O] |
| -Pro- | 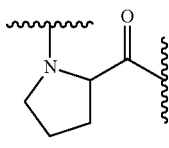 [SMILES: *C(=O)C1CCCN1*] |

The abbreviation "Ac-" is used in this description to name the acetyl group ($CH_3$—CO—) and the abbreviation "Palm-" is used to name the palmitoyl group ($CH_3$—$(CH_2)_{14}$—CO—).

The term "non-cyclic aliphatic group" is used in this invention to cover, for example and not restricted to, linear or branched alkyl, alkenyl and alkynyl groups.

The term "alkyl group" relates to a saturated, linear or branched group, which has between 1 and 24, preferably between 1 and 16, more preferably between 1 and 14, even more preferably between 1 and 12, and even more preferably still between 1, 2, 3, 4, 5 or 6 carbon atoms and which is bound to the rest of the molecule by a simple bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon double bonds, preferably with 1, 2 or 3 carbon-carbon double bonds, conjugated or unconjugated, which is bound to the rest of the molecule through a single bond, including, for example and not restricted to, the vinyl, oleyl, linoleyl and similar groups.

The term "alkynyl group" refers to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon triple bonds, preferably with 1, 2 or 3 carbon-carbon triple bonds, conjugated or unconjugated, which is bound to the rest of the molecule through a single bond, including, for example and not restricted to, the ethinyl group, 1-propinyl, 2-propinyl, 1-butinyl, 2-butinyl, 3-butinyl, pentinyl, such as 1-pentinyl and similar groups.

The term "alicyclic group" is used in this invention to cover, for example and not restricted to, cycloalkyl or cycloalkenyl or cycloalkynyl groups.

The term "cycloalkyl" relates to a saturated mono- or polycyclic aliphatic group which has between 3 and 24, preferably between 3 and 16, more preferably between 3 and 14, even more preferably between 3 and 12, even more preferably still 3, 4, 5 or 6 carbon atoms and which is bound to the rest of the molecule through a single bond, including, for example and not limited to, cyclopropyl, cyclobutyl, cyclopentyl, cyclohexyl, cycloheptyl, methyl cyclohexyl, dimethyl cyclohexyl, octahydroindene, decahydronaphthalene, dodecahydro-phenalene and similar.

The term "cycloalkenyl" relates to a non-aromatic mono- or polycyclic aliphatic group which has between 5 and 24, preferably between 5 and 16, more preferably between 5 and 14, even more preferably between 5 and 12, even more preferably still 5 or 6 carbon atoms, with one or more carbon-carbon double bonds, preferably with 1, 2 or 3 carbon-carbon double bonds, conjugated or unconjugated, which is bound to the rest of the molecule through a single bond, including, for example and not restricted to, the cyclopent-1-en-1-yl group and similar groups.

The term "cycloalkynyl" relates to a non-aromatic mono- or polycyclic aliphatic group which has between 8 and 24, preferably between 8 and 16, more preferably between 8 and 14, even more preferably between 8 and 12, even more preferably still 8 or 9 carbon atoms, with one or more carbon-carbon triple bonds, preferably with 1, 2 or 3 carbon-carbon triple bonds, conjugated or unconjugated, which is bound to the rest of the molecule through a single bond, including, for example and not restricted to, the cyclooct-2-yn-1-yl group and similar.

The term "aryl group" relates to an aromatic group which has between 6 and 30, preferably between 6 and 18, more preferably between 6 and 10, even more preferably 6 or 10 carbon atoms, which comprises 1, 2, 3 or 4 aromatic rings, bound by a carbon-carbon bond or fused, and which is bound to the rest of the molecule through a single bond, including, for example and not restricted to, phenyl, naphthyl, diphenyl, indenyl, phenanthryl or anthranyl among others.

The term "aralkyl group" relates to an alkyl group substituted by an aromatic group, with between 7 and 24 carbon atoms and including, for example and not restricted to, —$(CH_2)_{1-6}$-phenyl, —$(CH_2)_{1-6}$-(1-naphtyl), —$(CH_2)_{1-6}$-(2-naphtyl), —$(CH_2)_{1-6}$—CH(phenyl)$_2$ and similar.

The term "heterocyclic group" relates to a 3-10 member heterocycyl or hydrocarbon ring, in which one or more of the ring atoms, preferably 1, 2 or 3 of the ring atoms, is a different element to carbon, such as nitrogen, oxygen or sulfur and may be saturated or unsaturated. For the purposes of this invention, the heterocyclyl can be a cyclic, monocyclic, bicyclic or tricyclic system which may include fused ring systems; and the nitrogen, carbon or sulfur atoms can be optionally oxidized in the heterocyclyl radical; the nitrogen atom can optionally be quaternized; and the heterocyclyl radical may be partially or completely saturated or may be aromatic. With increasing preference, the term heterocyclic relates to a 5 or 6 member ring.

The term "heteroarylalkyl group" relates to an alkyl group substituted with a substituted or unsubstituted aromatic heterocyclyl group, the alkyl group having from 1 to 6 carbon atoms and the aromatic heterocyclyl group between 2 and 24 carbon atoms and from 1 to 3 atoms other than carbon and including, for example and not restricted to, —$(CH_2)_{1-6}$-imidazolyl, —$(CH_2)_{1-6}$-triazolyl, —$(CH_2)_{1-6}$-thienyl, —$(CH_2)_{1-6}$-furyl, —$(CH_2)_{1-6}$-pyrrolidinyl and similar.

As used in this technical area, there may be a degree of substitution on the groups defined above. Thus, there can be substitution in any of the groups of this invention. The references in this document to groups substituted in the groups of this invention indicate that the radical specified can be substituted in one or more available positions by one or more substituents, preferably in 1, 2 or 3 positions, more preferably in 1 or 2 positions, even more preferably in 1 position. These substituents include, for example and not restricted to, alkyl $C_1$-$C_4$; hydroxyl; alcoxyl $C_1$-$C_4$; amino; aminoalkyl $C_1$-$C_4$; carbonyloxyl $C_1$-$C_4$; oxycarbonyl $C_1$-$C_4$; halogen such as fluorine, chlorine, bromine and iodine; cyano; nitro; azido; alkylsulfonyl $C_1$-$C_4$; thiol; alkylthio aryloxyl such as phenoxyl; —$NR_b(C=NR_b)NR_bR_c$; where $R_b$ and $R_c$ are selected independently from the group consisting of H, alkyl $C_1$-$C_4$, alkenyl $C_2$-$C_4$, alkynyl $C_2$-$C_4$, cycloalkyl $C_3$-$C_{10}$, aryl $C_6$-$C_{18}$, aralkyl $C_7$-$C_{17}$, 3-10-membered-heterocyclyl or protective group of the amino group.

Compounds of the Invention

The compounds of the invention are defined by the general formula (I)

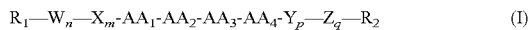

$$R_1—W_n—X_m\text{-}AA_1\text{-}AA_2\text{-}AA_3\text{-}AA_4\text{-}Y_p—Z_q—R_2 \quad (I)$$

their stereoisomers, mixtures thereof and/or their cosmetically or pharmaceutically acceptable salts, characterized in that:

$AA_1$ is -His-;
$AA_2$ is selected from the group consisting of -His-, -Leu- and -Pro-;
$AA_3$ is -Leu-;
$AA_4$ is selected from the group consisting of -Arg- and -Asn-;
W, X, Y and Z are independently selected from amongst themselves from the group consisting of codified amino acids and non-codified amino acids;
n, m, p and q are independently selected from amongst themselves and have a value between 0 and 1;
n+m+p+q is less or equal to 2;
$R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;
$R_2$ is selected from the group consisting of —$NR_3R_4$, —$OR_3$ and —$SR_3$, wherein $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl;
with the proviso that when $AA_2$ is -Leu-, $AA_4$ is -Asn-, Y is -Gln- then Z is not -Leu-;
and with the proviso that when $AA_2$ is -His-, $AA_4$ is -Arg-, Y or Z are -Tyr- then p+q is not 1.

The $R_1$ and $R_2$ groups are bound to the amino-terminal (N-terminal) and carboxy-terminal (C-terminal) ends of the peptide sequences respectively.

According to a preferred embodiment of this invention, $R_1$ is selected from the group consisting of H or $R_5$—CO—, wherein $R_5$ is selected from the group consisting of substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocycyl with 3-10 ring members, and substituted or unsubstituted heteroarylalkyl of 2 to 24 carbon atoms and 1 to 3 atoms other than carbon and an alkyl chain of 1 to 6 carbon atoms. More preferably, $R_1$ is selected from H, acetyl, tert-butanoyl, hexanoyl, 2-methylhexanoyl, cyclohexancarboxyl, octanoyl, decanoyl, lauroyl, myristoyl, palmitoyl, stearoyl, oleoyl and linoleoyl. Even more preferably, $R_1$ is H, acetyl, lauroyl, myristoyl or palmitoyl. In an even more preferred embodiment, $R_1$ is acetyl or palmitoyl.

According to another preferred embodiment, $R_2$ is —$NR_3R_4$, —$OR_3$ or —$SR_3$, wherein $R_3$ and $R_4$ are independently selected from the group consisting of H, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl with 3-10 ring members and substituted or unsubstituted heteroarylalkyl of 2 to 24 carbon atoms and 1 to 3 atoms other than carbon where the alkyl chain is 1 to 6 carbon atoms. Optionally, $R_3$ and $R_4$ can be bound through a saturated or unsaturated carbon-carbon bond, forming a cycle with the nitrogen atom. More preferably $R_2$ is —$NR_3R4$, or —$OR_3$. More preferably $R_3$ and $R_4$ are selected from the group consisting of H, methyl, ethyl, hexyl, dodecyl or hexadecyl. Even more preferably $R_3$ is H and $R_4$ is selected from the group consisting of H, methyl, ethyl, hexyl, dodecyl or hexadecyl. According to an even more preferable embodiment, $R_2$ is selected from —OH and —$NH_2$.

According to another embodiment of this invention $R_1$ is selected from the group consisting of H, acetyl, lauroyl, myristoyl or palmitoyl, $AA_2$ is -L-Leu-, $AA_4$ is -L-Arg-, and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —OH. Even more preferably, n, m, p and q are 0.

According to another embodiment of this invention $R_1$ is selected from the group consisting of H, acetyl, lauroyl, myristoyl or palmitoyl, $AA_2$ is -L-Pro-, $AA_4$ is -L-Arg-, and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —OH. Even more preferably, n, m, p and q are 0.

Preferably, the compounds of formula (I) are selected from the group consisting of:
Palm-His-Leu-Leu-Arg-NH$_2$,
Palm-His-Leu-Leu-Arg-OH,
Ac-His-Leu-Leu-Arg-NH$_2$,
Ac-His-Leu-Leu-Arg-OH,
Ac-His-Leu-Leu-Arg-NH—(CH$_2$)$_{15}$—CH$_3$,
Palm-His-Leu-Leu-Asn-NH$_2$,
Palm-His-Leu-Leu-Asn-OH,
Ac-His-Leu-Leu-Asn-NH$_2$,
Ac-His-Leu-Leu-Asn-OH,
Ac-His-Leu-Leu-Asn-NH—(CH$_2$)$_{15}$—CH$_3$,
Palm-His-Pro-Leu-Arg-NH$_2$,
Palm-His-Pro-Leu-Arg-OH,
Ac-His-Pro-Leu-Arg-NH$_2$,
Ac-His-Pro-Leu-Arg-OH,
Ac-His-Pro-Leu-Arg-NH—(CH$_2$)$_{15}$—CH$_3$,
Palm-His-Pro-Leu-Asn-NH$_2$,
Palm-His-Pro-Leu-Asn-OH,
Ac-His-Pro-Leu-Asn-NH$_2$,
Ac-His-Pro-Leu-Asn-OH,
Ac-His-Pro-Leu-Asn-NH—(CH$_2$)$_{15}$—CH$_3$,
Palm-His-His-Leu-Arg-NH$_2$,
Palm-His-His-Leu-Arg-OH,
Ac-His-His-Leu-Arg-NH$_2$,
Ac-His-His-Leu-Arg-OH,
Ac-His-His-Leu-Arg-NH—(CH$_2$)$_{15}$—CH$_3$,
Palm-His-His-Leu-Asn-NH$_2$,
Palm-His-His-Leu-Asn-OH,
Ac-His-His-Leu-Asn-NH$_2$,
Ac-His-His-Leu-Asn-OH,
Ac-His-His-Leu-Asn-NH—(CH$_2$)$_{15}$—CH$_3$,
Ac-Gly-Gly-His-Pro-Leu-Asn-OH,
Ac-His-His-Leu-Asn-Ala-Leu-OH,
Ac-Gly-His-His-Leu-Asn-Ala-OH,
their stereoisomers, mixtures thereof and/or their cosmetically or pharmaceutically acceptable salts.

The peptides of this invention can exist as stereoisomers or mixtures of stereoisomers; for example, the amino acids which form them can have an L-, D-configuration or be racemic independently of one another. Therefore, it is possible to obtain isomeric mixtures as well as racemic mixtures or diastereomeric mixtures, or pure diastereomers or enantiomers, depending on the number of asymmetric carbons and which isomers or isomeric mixtures are present. The preferred structures of the peptides of the invention are pure isomers, i.e., enantiomers or diastereomers.

For example, when it is indicated that AA$_1$ can be -His-, it is understood that AA$_1$ is selected from -L-His-, -D-His- or mixtures of both, racemic or non-racemic. Likewise, when it is said that AA$_2$ can be -Leu-, it is understood that it can be -L-Leu-, -D-Leu- or mixtures of both, racemic or non-racemic. The preparation processes described in this document allow the person skilled in the art to obtain each of the stereoisomers of the peptide of the invention by choosing the amino acid with the appropriate configuration.

In the context of this invention, the term "uncodified amino acids" relates to those amino acids not codified by the genetic code, natural or unnatural, such as and not restricted to, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, astatine, β-alanine, norleucine, N-methyl amino acids, β-amino acids or γ-amino acids among others, as well as their derivatives. A list of unnatural amino acids can be found in the article "Unusual amino acids in peptide synthesis" by D. C. Roberts and F. Vellaccio, in The Peptides, Vol. 5 (1983), Chapter VI, Gross E. and Meienhofer J., Eds., Academic Press, New York, USA or in the commercial catalogues of the companies specialized in the field, such as PolyPeptide Laboratories, Bachem, Novabiochem, Sigma-Aldrich, Peptides International, Advanced ChemTech, Chem-Impex, Maybridge Chemical, Chirotech Technology, Peninsula Laboratories or RSP Amino Acid Analogues among others.

In the context of this invention when n, m, p or q are different to 0 it is clearly understood that the nature of W, X, Y and/or Z does not make the activity of the peptides of this invention difficult, but it either contributes to the stimulation of heat shock protein synthesis or it has no effect on it.

In the context of this invention there are also cosmetically or pharmaceutically acceptable salts of the peptides provided by this invention. The term "cosmetically or pharmaceutically acceptable salts" means a salt admitted for its use on animals and, more particularly, human beings, and includes the salts used to form base addition salts, whether inorganic, for example and not restricted to, lithium, sodium, potassium, calcium, magnesium, manganese, copper, zinc or aluminum among others; whether organic such as and not restricted to, ethylamine, diethylamine, ethylenediamine, ethanolamine, diethanolamine, arginine, lysine, histidine or piperazine among others; or acid addition salts, whether organic, for example and not restricted to, acetate, citrate, lactate, malonate, maleate, tartrate, fumarate, benzoate, aspartate, glutamate, succinate, oleate, trifluoroacetate, oxalate, pamoate or gluconate among others; or inorganic, for example and not restricted to chloride, sulfate, borate or carbonate among others. The nature of the salt is not critical, provided that it is cosmetically and pharmaceutically acceptable. Cosmetically and pharmaceutically acceptable salts of the peptides of the invention can be obtained by conventional methods, well known in the prior art [Berge S. M., Bighley L. D. and Monkhouse D. C. (1977) *"Pharmaceutical Salts" J. Pharm. Sci.* 66:1-19].

An aspect of this invention relates to a peptide of general formula (I), its stereoisomers, mixtures thereof, and/or its cosmetically or pharmaceutically acceptable salts, as described in this invention, for the treatment and/or care of the skin, mucous membranes and/or hair.

In another particular aspect, this invention relates to a peptide of general formula (I), its stereoisomers, mixtures thereof, and/or its cosmetically or pharmaceutically acceptable salts, as described in this invention, for the treatment and/or care of those conditions, disorders and/or diseases which are improved or prevented by the stimulation of Hsp protein synthesis, specifically proteins from the Hsp family with a molecular weight between 20 kDa and 110 kDa, more specifically with a molecular weight between 40 kDa and 100 kDa and even more specifically Hsp proteins with a molecular weight comprised between 60 kDa and 80 kDa and in particular the Hsp with a molecular weight of 70 kDa or Hsp70.

In a preferred embodiment, the conditions, disorders and/or diseases which are improved or prevented by a stimulation of heat shock protein synthesis are selected from the group consisting of epidermolysis bullosa and alopecia, including alopecia caused by chemotherapy treatment for cancer.

In another particular aspect, this invention relates to a peptide of general formula (I), its stereoisomers, mixtures thereof, and/or its cosmetically or pharmaceutically acceptable salts, as described in this invention, for the treatment and/or care of the skin, mucous membranes and/or hair, which reduces, delays, and/or prevents cell damage induced by UV radiation, thermal stress, oxidative stress, osmotic shock, inflammation, hypoxia, exposure to pollutants, lack of nourishment and lack of hydration.

In another aspect, this invention relates to a peptide of general formula (I), its stereoisomers, mixtures thereof, and/or its cosmetically or pharmaceutically acceptable salts, as described in this invention, for the treatment and/or care of the skin, mucous membranes and/or hair, which reduces, and/or prevents the signs of aging and/or photoaging.

In another aspect, this invention relates to a peptide of general formula (I), its stereoisomers, mixtures thereof, and/or its cosmetically or pharmaceutically acceptable salts, as described in this invention, for the treatment and/or care of the skin and/or mucous membranes, which stimulates healing and/or re-epithelialization of wounds, preferably those wounds that are a result of diabetes.

In another particular aspect, this invention relates to a peptide of general formula (I), its stereoisomers, mixtures thereof, and/or its cosmetically or pharmaceutically acceptable salts, as described in this invention, for the treatment and/or care of the skin and/or hair which delays and/or prevents hair loss or induces hair growth.

Processes of Preparation

The synthesis of the peptides of the invention, their stereoisomers or their cosmetically or pharmaceutically acceptable salts can be performed according to conventional methods, known in the prior art, such as solid phase peptide synthesis methods [Stewart J. M. and Young J. D. (1984) "Solid Phase Peptide Synthesis, 2nd edition" Pierce Chemical Company, Rockford, Ill.; Bodanzsky M. and Bodanzsky A. (1984) "The practice of Peptide Synthesis" Springer Verlag, New Cork; Lloyd-Williams P., Albericio F. and Giralt E. (1997) "Chemical Approaches to the Synthesis of Peptides and Proteins" CRC, Boca Raton, Fla., USA], synthesis in solution, a combination of the methods for solid phase synthesis and solution synthesis or enzymatic synthesis [Kullmann W (1980) "Proteases as catalysts for enzymic syntheses of opioid peptides" J. Biol. Chem. 255:8234-8238]. The peptides can also be obtained by fermentation of a bacterial strain, genetically engineered or not, in order to produce the desired sequences, by controlled hydrolysis of proteins of animal or vegetable origin, preferably vegetable origin, to release peptide fragments containing at least the desired sequence.

For example, a method of obtaining the peptides of the invention of formula (I) comprises the steps of:
  coupling an amino acid with the N-terminal end protected and the C-terminal end free, onto an amino acid with the N-terminal end free and the C-terminal end protected or bound to a solid support;
  removing the protective group of the N-terminal end;
  repetition of the sequence of coupling and removal of the protective group of the N-terminal end until the desired peptidic sequence is obtained;
  removal of the protective group of the C-terminal end or cleavage from the solid support.

Preferably, the C-terminal end is bound to a solid support and the process is conducted on solid phase and, therefore, includes the coupling of an amino acid with the N-terminal end protected and the C-terminal end free onto an amino acid with the N-terminal end free and the C-terminal end bound to a polymer support; removal of the protective group of the N-terminal end; and repetition of this sequence as many times as is necessary to obtain a peptide of the desired length, and finally followed by cleaving the synthesized peptide from the original polymer support.

The functional groups of the side chains of the amino acids are adequately protected with temporary or permanent protective groups throughout synthesis, and can be deprotected simultaneously or orthogonally to the process of cleaving the peptide from the polymer support.

Alternatively, solid phase synthesis can be carried out by a convergent strategy coupling a peptide onto the polymer support or onto a peptide or onto an amino acid previously bound to the polymer support. Convergent synthesis strategies are widely known to the person skilled in the art and are described in Lloyd-Williams P., Albericio F. and Giralt E. in "Convergent solid-phase peptide synthesis" (1993) Tetrahedron 49:11065-11133.

The process can comprise the additional stages of deprotection of the N-terminal and/or C-terminal ends and/or cleavage of the peptide from the polymer support in a different order, using standard processes and conditions known in the prior art, after which the functional groups of these ends can be modified. The optional modification of the N-terminal and/or C-terminal ends can be carried out with the peptide of formula (I) bound to the polymeric support or once the peptide has been cleaved from the polymeric support.

Optionally, $R_1$ may be introduced by the reaction of the N-terminal end of the peptide of the invention with a compound $R_1$-J, wherein $R_1$ is as described above and J is a leaving group for example and not restricted to, the tosyl group, the mesyl group and halogen groups among others; through a nucleophilic substitution reaction, in the presence of an adequate base and solvent, wherein the fragments that have the functional groups not involved in the N—C bond formation are suitably protected with temporary or permanent protective groups.

Optionally and/or additionally, the $R_2$ radicals can be introduced by the reaction of a compound $HR_2$ wherein $R_2$ is –$OR_3$, —$NR_3R_4$ or —$SR_3$, with a complementary fragment which corresponds to the peptide of formula (I) in which $R_2$ is —OH in the presence of an adequate solvent and a base such as, N,N-diisopropylethylamine (DIEA) or triethylamine or an additive such as 1-hydroxybenzotriazole (HOBt) or 1-hydroxyazabenzotriazole (HOAt) and a dehydrating agent, such as a carbodiimide, a uronium salt, a phosphonium salt or amidinium salt, among others, or by prior formation of an acyl halide with, for example, thionyl chloride, and thereby obtaining a peptide according to the general formula (I) invention, wherein the fragments that have the functional groups not involved in the N—C bond formation are suitably protected with temporary or permanent protective groups, or alternatively other $R_2$ radicals may be introduced by simultaneous incorporation to the peptide cleavage process from the polymeric support.

A person skilled in the art would easily understand that the deprotection/cleavage steps of the C-terminal and N-terminal ends and their subsequent derivatization can be performed in a different order, according to the processes known in the prior art [Smith M. B. and March J. (1999) "March's Advanced Organic Chemistry Reactions, Mechanisms and Structure", 5th Edition, John Wiley & Sons, 2001].

The term "protective group" relates to a group which blocks a functional organic group and can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (CIZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), Trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxocyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (trityl ester, Trt), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino) benzyl ester (Dmab), among others; preferred protective groups of the invention are the All, tBu, cHx, Bzl and Trt esters.

The side chains of the trifunctional amino acids can be protected during the synthetic process with temporary or permanent protective groups orthogonal to the protective groups of the N-terminal and C-terminal ends.

The guanidine group of the arginine side chain can be protected with the nitro group, allyloxycarbonyl (Alloc), para-toluenesulfonyl (tosyl, Tos), 2,2,5,7,8-pentamethylchroman-6-sulfonyl (Pmc), 2,2,4,6,7-pentamethyldihydrobenzofuran-5-sulfonyl (Pbf) or 4-methoxy-2,3,6-trimethylbenzenesulfonyl (Mtr), among others; the imidazolyl group of the histidine side chain can be protected with the tosyl group (Tos), the tert-butyloxycarbonyl group (Boc), the trityl group (Trt), the methoxytrityl group (Mtt) or the 2,4-dinitrophenyl group (Dnp) among others; and the amide group of the asparagine side chain can be protected with the trityl group (Trt) or the xanthyl group (Xan) or is used unprotected.

In a preferred embodiment, the protective group strategy used is the strategy wherein the amino groups are protected by Boc, the carboxyl groups are protected by Bzl, cHx or All esters, the arginine side chain is protected by Mtr or Tos, the asparagine side chain is used unprotected and the histidine side chain is protected by Tos or Dnp.

In another preferred embodiment, the protective group strategy used is the strategy wherein the amino groups are protected by Fmoc, the carboxyl groups are protected by tBu, All or Trt esters, the arginine side chain is protected by Pmc or Pbf, the asparagine side chain by Trt and the hisitidine side chain by Trt or Mtt.

Examples of these and other additional protective groups, their introduction and removal, can be found in the literature [Greene T. W. and Wuts P. G. M., (1999) "*Protective groups in organic synthesis*" John Wiley & Sons, New York; Atherton B. and Sheppard R. C. (1989) "*Solid Phase Peptide Synthesis: A practical approach*" IRL Oxford University Press]. The term "protective groups" also includes the polymeric supports used in solid phase synthesis.

When synthesis takes place totally or partially on solid phase, the possible solid supports used in the process of the invention can involve polystyrene supports, polyethylene glycol grafted to polystyrene and similar, for example and not restricted to, p-methylbenzhydrylamine (MBHA) resins [Matsueda G. R. and Stewart J. M. (1981) "*A p-methylbenzhydrylamine resin for improved solid-phase synthesis of peptide amides*" Peptides 2:45-50], 2-chlorotrityl resins [Barbs K., Gatos D., Kallitsis J., Papaphotiu G., Sotiriu P., Wenqing Y. and Schäfer W. (1989) "*Darstellung geschützter Peptid-Fragmente unter Einsatz substituierter Triphenylmethyl-Harze*" Tetrahedron Lett. 30:3943-3946; Barlos K., Gatos D., Kapolos S., Papaphotiu G., Schäfer W. and Wenqing Y. (1989) "*Veresterung von partiell geschützten Peptid-Fragmenten mit Harzen. Einsatz von 2-Chlorotritylchlorid zur Synthese von Leu1-Gastrin I*" Tetrahedron Lett. 30:3947-3951], TentaGel® resins (Rapp Polymere GmbH), ChemMatrix® resins (Matrix Innovation, Inc) and similar, which may or may not include a labile linker, such as 5-(4-aminomethyl-3,5-dimethoxy phenoxy)valeric acid (PAL) [Albericio F., Kneib-Cordonier N., Biancalana S., Gera L., Masada R. I., Hudson D. and Barany G. (1990) "*Preparation and application of the 5-(4-(9-fluorenylmethyloxycarbonyl)aminomethyl-3,5-dimethoxy phenoxy)valeric acid (PAL) handle for the solid-phase synthesis of C-terminal peptide amides under mild conditions*" J. Org. Chem. 55:3730-3743], 2-(AM) [Rink H. (1987) "*Solid-phase synthesis of protected peptide fragments using a trialkoxy-diphenyl-methylester resin*" Tetrahedron Lett. 28:3787-3790], Wang [Wang S. S. (1973) "*p-Alkoxybenzyl Alcohol Resin and p-Alkoxybenzyloxycarbonylhydrazide Resin for Solid Phase Synthesis of Protected Peptide Fragments*" J. Am. Chem. Soc. 95:1328-1333] and similar, allowing the simultaneous deprotection and cleavage of the peptide from the polymeric support.

Cosmetic or Pharmaceutical Compositions

To this regard, another aspect of the invention is a cosmetic or pharmaceutical composition which comprises at least a peptide of general formula (I), its stereoisomers, mixtures thereof, and/or its cosmetically or pharmaceutically acceptable salts together with at least one cosmetically or pharmaceutically acceptable adjuvant. These compositions can be prepared by conventional means known to persons skilled in the art ["*Harry's Cosmeticology*", Eight edition (2000) Rieger M. M., ed., New York Chemical Pub., NY, US; "*Remington: The Science and Practice of Pharmacy*", Twentieth edition (2003) Genaro A. R., ed., Lippincott Williams & Wilkins, Philadelphia, US].

The peptides of this invention have variable solubility in water, according to the nature of their sequence or any possible modifications in the N-terminal and/or C-terminal ends. Therefore, the peptides of this invention can be incorporated into the compositions by aqueous solution, and those which are not soluble in water can be solubilized in cosmetically or pharmaceutically acceptable conventional solvents for example and not restricted to, ethanol, propanol, isopropanol, propylene glycol, glycerine, butylene glycol or polyethylene glycol or any combination thereof.

The cosmetically or pharmaceutically effective amount of the peptides of the invention which should be administered, as well as their dosage, will depend on numerous factors, including age, state of the patient, the nature or severity of the condition, disorder or disease to be treated, cared for and/or prevented, the route and frequency of administration and of the particular nature of the peptides to be used.

"Cosmetically and pharmaceutically effective amount" is understood to mean a non-toxic but sufficient amount of the peptide or peptides of the invention to provide the desired effect. The peptides of the invention are used in the cosmetic or pharmaceutical composition of this invention in cosmetically or pharmaceutically effective concentrations to achieve the desired effect; in a preferred form versus the total weight of the composition, between 0.00000001% (in weight) and 20% (in weight); preferably between 0.000001% (in weight) and 20% (in weight), more preferably between 0.0001% (in weight) and 10% (in weight) and even more preferably between 0.0001% (in weight) and 5% (in weight).

The peptides of the invention can also be incorporated into cosmetic or pharmaceutical delivery systems and/or sustained release systems.

The term "delivery systems" relates to a diluent, adjuvant, excipient or carrier with which the peptide of the invention is administered. These cosmetic or pharmaceutical carriers can be liquids, such as water, oils or surfactants, including those of petroleum, animal, vegetable or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. In "Remington's Pharmaceutical Sciences" by E. W. Martin diluents, adjuvants or excipients are described as appropriate carriers.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems are liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules and nanocapsules, as well as microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles and microemulsions, more preferably water-in-oil microemlusions with an internal structure of reverse micelle.

Sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, orally or parenterally, including nasal, rectal or subcutaneous implantation or injection, or direct implantation or injection into a specific body part, and preferably should release a relatively constant quantity of the peptides of the invention. The amount of peptide contained in the sustained release system will depend, for example, on where the composition is to be administered, the kinetics and duration of the release of the peptide of the invention, as well as the nature of the condition, disorder and/or disease to be treated and/or cared for.

The peptides of this invention can also be adsorbed on solid organic polymers or solid mineral supports such as and not restricted to, talc, bentonite, silica, starch or maltodextrin among others.

The compositions which contain the peptides of the invention can also be incorporated into fabrics, non-woven fabrics and medical devices which are in direct contact with the skin: thus releasing the peptides of the invention whether by biodegradation of the binding system to the fabric, non-woven fabric or medical device, or by the friction between them and the body, due to body moisture, the skin's pH or body temperature. Furthermore, the fabrics and non-woven fabrics can be used for making garments that are in direct contact with the body. Preferably, the fabrics, non-woven fabrics and medical devices containing peptides of the invention are used for the treatment and/or care of those conditions, disorders and/or diseases which are improved or prevented by a stimulation of Hsp synthesis.

Examples of fabrics, non-woven fabrics, garments, medical devices and means for immobilizing the peptides to them, among which are the delivery systems and/or the sustained release systems described above, can be found in literature and are known in the prior art [Schaab C. K. (1986) "Impregnating Fabrics With Microcapsules", HAPPI May 1986; Nelson G. (2002) "Application of microencapsulation in textiles" Int. J. Pharm. 242:55-62; "Biofunctional Textiles and the Skin" (2006) Curr. Probl. Dermatol. v. 33, Hipler U. C. and Elsner P., eds. S. Karger A G, Basel, Switzerland; Malcom R. K.; McCullagh S. D., Woolfson A. D., Gorman S. P., Jones D. S. y Cuddy J. (2004) "Controlled release of a model antibacterial drug from a novel self-lubricating silicone biomaterial" J. Cont. Release 97:313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, micro-electric patches and/or face masks.

The cosmetic or pharmaceutical compositions which contain the peptides of this invention, their stereoisomers, mixtures thereof and/or their cosmetically or pharmaceutically acceptable salts, can be used in different types of compositions of topical or transdermal application, optionally including cosmetically or pharmaceutically acceptable excipients necessary for formulating the desired administration form [Faulí i Trillo C. (1993) in "Tratado de Farmacia Galénica", Luzán 5, S. A. Ediciones, Madrid].

The compositions of topical or transdermal application can be produced in any solid, liquid or semisolid formulation, such as and not restricted to, creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories such as and not restricted to, bandages, gauzes, t-shirts, socks, tights, underwear, girdles, gloves, diapers, sanitary napkins, dressings, bedspreads, wipes, adhesive patches, non-adhesive patches, occlusive patches, micro-electric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders among others.

The cosmetic and pharmaceutical compositions of the invention may include agents which increase the percutaneous absorption of the peptides of this invention, such as and not restricted to, dimethylsulfoxide, dimethylacetamide, dimethylformamide, surfactants, azone(1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the peptide of the invention. The application area will be determined by the nature of the condition, disorder and/or disease to be treated and/or cared for.

Furthermore, the cosmetic compositions containing the peptides of this invention, their stereoisomers or their cosmetically or pharmaceutically acceptable salts can be used in different types of formulations for oral administration, preferably in the form of oral cosmetics and pharmaceutical drugs, such as and not restricted to, capsules, including gelatin capsules, soft capsules, hard capsules, tablets, including sugar coated tablets, powders, granules, chewing gum, solutions, suspensions, emulsions, syrups, polysaccharide films, jellies or gelatins, and any other form known by the person skilled in the art. In particular, the peptides of the invention can be incorporated into any form of functional food or fortified food, such as and not restricted to, dietary bars or compact or non-compact powders. These powders can be dissolved in water, juices, soda, dairy products, soya derivatives or can be incorporated into dietary bars. The peptides of this invention can be formulated with common excipients and adjuvants for oral compositions or food supplements, such as and not restricted to, fat components, aqueous components, humectants, preservatives, texturizing agents, flavors, aromas, antioxidants and colorants common in the food industry.

Cosmetic or pharmaceutical compositions containing the peptides of the invention, their stereoisomers, mixtures thereof and/or their cosmetically or pharmaceutically acceptable salts can also be administered by topical or transdermal route, as well as by any other appropriate route, as for example oral or parenteral route, for which they will include the pharmaceutically acceptable excipients necessary for the formulation of the desired administration form. In the context of this invention, the term "parenteral" includes nasal, auricular, ophthalmic, rectal, urethral, vaginal, subcutaneous, intradermal, intravascular injections, such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A review of the different pharmaceutical forms of administration of the active ingredients and excipients necessary for obtaining them can be found, for example, in the "*Tratado de Farmacia Galénica*", C. Faulí i Trillo, 1993, *Luzán* 5, S. A. Ediciones, Madrid.

Among the cosmetically or pharmaceutically acceptable adjuvants contained in the cosmetic or pharmaceutical compositions described in this invention include additional ingredients commonly used in compositions for the treatment and/or care of the skin, mucous membranes and/or hair such as and not restricted to, heat shock proteins, other heat shock protein synthesis stimulating agents, acetylcholine-receptor aggregation inhibitors, muscle contraction inhibiting agents, anticholinergic agents, elastase inhibiting agents, matrix metalloproteinase inhibiting agents, melanin synthesis stimulating or inhibiting agents, whitening or depigmenting agents, propigmenting agents, self-tanning agents, anti-aging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners such as humectants, substances that retain moisture, alpha hydroxyacids, beta hydroxyacids, moisturizers, epidermal hydrolytic enzymes, vitamins, amino acids, proteins, pigments or colorants, dyes, gelling polymers, thickeners, surfactants, softening agents, anti-wrinkle agents, agents able to reduce or treat bags under the eyes, exfoliating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, such as for example collagen synthesis-stimulating agents, elastin synthesis-stimulating agents, decorin synthesis-stimulating agents, laminin synthesis-stimulating agents, defensin synthesis-stimulating agents, aquaporin synthesis-stimulating agents, hyaluronic acid synthesis-stimulating agents, fibronectin synthesis-stimulating agents, sirtuin synthesis-stimulating agents, agents stimulating the synthesis of lipids and components of the stratum corneum (ceramides, fatty acids, etc.), agents that inhibit collagen degradation, other agents that inhibit elastin degradation, agents that inhibit serine proteases such as cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, glycosaminoglycan synthesis-stimulating agents, antihyperkeratosis agents, comedolytic agents, antipsoriasis agents, DNA repair agents, DNA protecting agents, stabilizers, anti-itching agents, agents for the treatment and/or care of sensitive skin, firming agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating re-epithelialization, coadjuvant re-epithelialization agents, cytokine growth factors, calming agents, anti-inflammatory and/or analgesic agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, hair loss retardant agents, preservatives, perfumes, chelating agents, vegetable extracts, essential oils, marine extracts, agents obtained from a bio-fermentation process, mineral salts, cell extracts and sunscreens (organic or mineral photoprotective agents active against ultraviolet A and/or B rays) among others, provided they are physically and chemically compatible with the other components of the composition and especially with the peptides of general formula (I) contained in the composition of this invention. Furthermore, the nature of these additional ingredients should not unacceptably alter the benefits of the peptides of this invention. The nature of these additional ingredients can be synthetic or natural, such as vegetable extracts, or obtained by a biotechnological process or a combination of a synthetic process and a biotechnological process. Additional examples can be found in the *CTFA International Cosmetic Ingredient Dictionary & Handbook*, 12*th Edition* (2008). In the context of this invention, biotechnological process is understood to be any process which produces the active ingredient, or part of it, in an organism, or in a part of it.

An additional aspect of this invention relates to a cosmetic or pharmaceutical composition containing a cosmetically or pharmaceutically effective amount of at least one peptide according to the general formula. (I), its stereoisomers, mixtures thereof and/or its cosmetically or pharmaceutically acceptable salts, and also a cosmetically or pharmaceutically effective amount of at least one extract, synthetic compound or bio-fermentation product which stimulates Hsp synthesis, such as and not restricted to, extracts of *Opuntia ficus indica, Salix alba, Lupinus* spp., *Secale cereale*, extracts of red algae of the genus *Porphyra*, extracts of crustaceans of the genus *Artemia*, jojoba seed oil, grape seed extracts, green tea extracts, geranylgeranylacetone, celastrol, zinc and its salts, 2-cyclopenten-1-one, proteasome inhibitors such as and not restricted to, bortezomib; prostaglandins and their derivatives, hydroxylamine and its derivatives such as and not restricted to, bimoclomol; chalcone and its derivatives, hyperosmotic agents such as and not restricted to, sorbitol and its derivatives, mannitol and its derivatives or glycerol and its derivatives, isosorbide, urea or salicylic acid and its derivatives among others, or mixtures thereof.

An additional aspect of this invention relates to a cosmetic or pharmaceutical composition containing a cosmetically or pharmaceutically effective amount of at least one peptide according to the general formula (I), its stereoisomers, mixtures thereof and/or its cosmetically or pharmaceutically acceptable salts, and also a cosmetically or pharmaceutically effective amount of at least one extract which is an anti-wrinkle agent and/or anti-aging agent such as and not restricted to, the extracts of *Vitis vinifera, Rosa canina, Curcuma longa, Iris pallida, Theobroma cacao, Ginkgo biloba, Leontopodium Alpinum* or *Dunaliella salina* among others or, in addition, at least one synthetic compound or bio-fermentation product which is an anti-wrinkle agent and/or an anti-aging agent such as and not restricted to Matrixyl® [INCI: Palmitoyl Pentapeptide-4], Matrixyl 3000® [INCI: Palmitoyl Tetrapeptide-7, Palmitoyl Oligopeptide], Essenskin™ [INCI: calcium hydroxymethionine], Renovage [INCI: teprenone] or Dermaxyl® [INCI: Palmitoyl Oligopeptide] marketed by Sederma, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (Ceratonia Siliqua) Gum] or Preregen® [INCI: Glycine Soja (Soybean) Protein, Oxido Reductases] marketed by Pentapharm/DSM, Myoxinol™ [INCI: Hydrolyzed Hibiscus Esculentus Extract], Syniorage™ [INCI: Acetyl Tetrapeptide-11], Dermican™ [INCI: Acetyl Tetrapeptide-9] or DN-AGE™ LS [INCI: *Cassia Alata* leaf Extract] marketed by Laboratoires Sérobiologiques/Cognis, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline™ [INCI proposal: Acetyl Hexapeptide-25], Aldenine® [INCI: Hydrolized wheat protein, hydrolized soy protein, Tripeptide-1], Preventhelia™ [INCI: Diaminopropionoyl Tripeptide-33], Decorinyl® [INCI: Tripeptide-10 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase™ [INCI proposal: Acetyl Tetrapeptide-30], Lipochroman-6 [INCI: Dimethylmethoxy Chromanol], Chromabright™ [INCI: Dimethylmethoxy Chromanyl Palmitate], Antarcticine® [INCI: Pseudoalteromonas Ferment Extract] or Vilastene™ [INCI: Lysine HCl, Lecithin, Tripeptide-10 Citrulline] marketed by Lipotec, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza Sativa* (Rice) Extract], D'Orientine™ IS [INCI: *Phoenix Dactylifera* (Date) Seed Extract], Phytoquintescine™ [INCI: Einkorn (*Triticum Monococcum*) Extract] or Quintescine™ IS [INCI: Dipeptide-4] marketed by Vincience/ISP, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: *Spilanthes Acmella* Flower Extract] or Gatuline® Age Defense 2 [INCI: *Juglans Regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium Innovations/Unipex Group, EquiStat [INCI: *Pyrus Malus* Fruit Extract, Glycine Soja Seed Extract] or Juvenesce [INCI: Ethoxydiglicol and Caprylic Triglycerid, Retinol, Ursolic Acid, Phytonadione, Ilomastat] marketed by Coletica/Engelhard/BASF, Ameliox [INCI: Carnosine, Tocopherol, *Silybum Marianum* Fruit Extract] or PhytoCellTec *Malus Domestica* [INCI: *Malus Domestica* Fruit Cell Culture] marketed by Mibelle Biochemistry, Bioxilift [INCI: *Pimpinella Anisum* Extract] or SMS Anti-Wrinkle® [INCI: *Annona Squamosa* Seed Extract] marketed by Silab, antagonists of the $Ca^{2+}$ channel such as and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes such as and not restricted to, photolyase, T4 endonuclease V, or chloride channel agonists among others.

In additional, this invention refers to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and, in addition, a cosmetically or pharmaceutically effective amount of at least one extract or combination of extracts which stimulate healing and/or re-epithelialization or coadjuvants of healing and/or re-epithelialization such as and not restricted to, the extracts of *Centella asiatica, Rosa moschata, Echinacea angustifolia, Symphytum officinal, Equisetum arvense, Hypericum perforatum, Mimosa tenuiflora, Aloe vera*, Polyplant® Epithelizing [INCI: *Calendula officinalis, Hypericum perforatum, Chamomilla recutita, Rosmarinus officinalis*] marketed by Provital, Cytokinol® LS 9028 [INCI: Hydrolyzed Casein, Hydrolyzed Yeast Protein, Lysine HCl] marketed by Laboratories Serobiologiques/Cognis or Deliner® [INCI: *Zea mays* (Corn) Kernel Extract] marketed by Coletica/Engelhard/BASF among others, and/or a cosmetically or pharmaceutically effective amount of at least one synthetic compound, extract or bio-fermentation product which stimulates healing and/or re-epithelialization such as and not restricted to, cadherins, integrins, selectins, hyaluronan acid receptors, immunoglobulins, fibroblast growth factor, connective tissue growth factor, platelet-derived growth factor, vascular endothelial growth factor, epidermal growth factor, insulin-like growth factor, keratinocyte growth factors, colony-stimulating factors, transforming growth factor-beta, tumor necrosis factor-alpha, interferons, interleukins, matrix metalloproteinases, protein tyrosine phosphatase receptors, Antarcticine® [INCI: Pseudoalteromonas Ferment Extract] or Decorinyl® [INCI: Tripeptide-10 Citrulline], marketed by Lipotec, among others, or a mixture thereof.

An additional aspect of this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and, in addition, a cosmetically or pharmaceutically effective amount of, at least one extract or combination of extracts delaying hair loss or inducing hair growth such as and not restricted to, extracts of *Tussilago farfara* or *Achillea millefolium*, and/or a cosmetically or pharmaceutically effective amount of at least one compound delaying hair loss or inducing hair growth, such as and not restricted to, nicotinic acid esters such as alkyl nicotinates $C_3$-$C_6$ such as methyl or hexyl nicotinate, benzyl nicotinate, or tocopherol nicotinate; steroid and nonsteroidal anti-inflammatory agents, such as and not restricted to, hydrocortisone, its salts and derivatives or niflumic acid; retinoids such as and not restricted to, all-trans-retinoic acid or tretinoin, isotretinoin, retinol or vitamin A, and its derivatives, such as acetate, palmitate, propionate, motretinide, etretinate and zinc trans retinoate; antibacterial agents such as and not restricted to, macrolides, pyranosides, and tetracycline, erythromycin; antagonists of calcium channels such as and not restricted to, cinnarizine and diltiazem; hormones such as and not restricted to, estriol, its analogues or tyrosine, its analogues and/or its salts; antiandrogen agents such as and not restricted to, oxendolone, spironolactone or diethylstilbestrol; anti-radicals such as and not restricted to, dimethyl sulfoxide; esterified oligosaccharides such as and not restricted to, those described in documents EP 0211610 and EP 0064012; derivatives of hexasaccharide acids such as and not restricted to glucose saccharide acid or those described in document EP 0375388; glucosidase inhibitors such as and not restricted to, D-glucaro-1,5-lactam or those described in document EP 0334586; glycosaminoglycan and proteoglycan inhibitors such as and not restricted to, L-galactono-1,4-lactone or those described in document EP 0277428; tyrosine kinase inhibitors such as and not restricted to, 1-amide-1-cyano(3,4-dihydroxyphenyl)ethylene or those described in document EP 0403238, diazoxides such as and not restricted to, 7-(acetylthio)-4',5'-dihydrospiro[androst-4-ene-17,2'-(3H)furan]-3-one, 3-methyl-7-chloro[2H]-1,2,4-benzothiadiazine or spiroxazone 1,1-dioxide; phospholipids such as and not restricted to, lecithin; salicylic acid and its derivatives, hydroxyl carboxylic or keto carboxylic acids and their esters, lactones and their salts; anthralin, eicosa-5,8,11-trienoic acids and their esters or amides or minoxidil and their derivatives among others, or mixtures thereof.

An additional aspect of this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and, in addition, a cosmetically or pharmaceutically effective amount of at least one sunscreen such as and not restricted to, anthranilates, cinnamates, salicylates, derivatives of dibenzoylmethane, derivatives of camphor, derivatives of triazine, derivatives of benzophenone, derivatives of β,β'-diphenylacrylate, derivatives of benzotriazole, derivatives of benzylmalonate, derivatives of benzimidazole, imidazolines, derivatives of benzoallyl, derivatives of the p-aminobenzoic acid, polymers and silicones, derivatives of alkyl styrenes, nanopigments of metallic oxides such as and not restricted to, titanium oxide or zinc oxide or filters based on carbon nanotubes among others, or mixtures thereof.

Another additional aspect of this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and, in addition, a cosmetically or pharmaceutically effective amount of at least one protein from the Hsp family, such as and not restricted to, Hsp70, including Hsp72 and Hsp73, Hsp60, Hsp27 or Hsp90 among others.

Applications

An aspect of this invention relates to the use of at least one of the peptides of general formula (I), its stereoisomers, mixtures thereof and/or its cosmetically or pharmaceutically acceptable salts in the preparation of a cosmetic or pharmaceutical composition for the treatment and/or care of skin, mucous membranes and/or hair.

Another aspect of this invention relates to the use of at least one of the peptides of general formula (I), its stereoisomers, mixtures thereof and/or its cosmetically or pharmaceutically acceptable salts in the preparation of a cosmetic or pharmaceutical composition for the treatment and/or care of those conditions, disorders and/or diseases which are improved or prevented by the stimulation of Hsp protein synthesis, specifically proteins from the Hsp family with a molecular weight between 20 kDa and 110 kDa, specifically of a molecular weight between 40 kDa and 100 kDa and even more specifically Hsp proteins with a molecular weight comprised between 60 kDa y 80 kDa, and in particular the Hsp with a molecular weight of 70 kDa or Hsp70.

In a preferred embodiment, the conditions, disorders and/or diseases which are improved or prevented by stimulation of heat shock protein stimulation are selected from the group formed by epidermolysis bullosa and alopecia, including alopecia caused by chemotherapy treatment for cancer.

According to a preferred embodiment, this invention relates to the use of a peptide of formula (I), its stereoisomers, mixtures thereof and/or its cosmetically or pharmaceutically acceptable salts in the preparation of a cosmetic or pharmaceutical composition for the treatment and/or care of the skin, mucous membranes and/or hair, which reduces, delays, and/or prevents cell damage induced by UV radiation, thermal stress, oxidative stress, osmotic shock, inflammation, hypoxia, exposure to pollutants, lack of nourishment and lack of hydration.

According to a preferred embodiment, this invention relates to the use of a peptide of formula (I), its stereoisomers, mixtures thereof and/or its cosmetically or pharmaceutically acceptable salts in the preparation of a cosmetic or pharmaceutical composition for the treatment and/or care of the skin and/or hair which reduces, delays or prevents the signs of aging and/or photoaging.

Likewise, this invention relates to the use of at least one of the peptides of formula (I), its stereoisomers, mixtures thereof and/or its cosmetically or pharmaceutically acceptable salts in the preparation of a cosmetic or pharmaceutical composition for the treatment and/or care of the skin, mucous membranes and/or hair, which stimulates healing and/or re-epithelialization of wounds, preferably those wounds that are a result of diabetes.

According to a preferred embodiment, this invention refers to the use of a peptide of formula (I), its stereoisomers, mixtures thereof and/or its cosmetically or pharmaceutically acceptable salts in the preparation of a cosmetic or pharmaceutical composition for the treatment and/or care of the skin and/or hair which delays and/or prevents hair loss or induces hair growth.

Examples of cosmetic or pharmaceutical compositions for the treatment and/or care of the skin, mucous membranes and/or hair include creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations, bandages, gauzes, t-shirts, socks, tights, underwear, girdles, gloves, diapers, sanitary napkins, dressings, bedspreads, wipes, adhesive patches, non-adhesive patches, occlusive patches, micro-electric patches or face masks, make-up products such as make-up foundation, such as fluid foundations and compact foundations, make-up removal lotions, make-up removal milks, under-eye concealers, eye shadows, lipsticks, lip protectors, lip gloss and powders among others.

The compositions containing the peptides of this invention can be applied to the skin or can be administered orally or parenterally as necessary to treat and/or care for a condition, disorder and/or disease.

The cosmetic or pharmaceutical compositions concerned in this invention can be applied to the skin by iontophoresis, sonophoresis, electroporation, micro-electric patches, mechanical pressure, osmotic pressure gradient, occlusive cure, microinjections or needle-free injections by means of pressure, such as injections by oxygen pressure, or any combination thereof, to achieve a greater penetration of the peptide of the invention.

An additional aspect of this invention relates to a method of treatment and/or care of the skin, mucous membranes and/or hair which comprises administering a cosmetically or pharmaceutically effective amount of at least one peptide of general formula (I), its stereoisomers, mixtures thereof and/or its cosmetically or pharmaceutically acceptable salts, preferably in the form of a cosmetic or a pharmaceutical composition containing them.

An additional aspect of this invention relates to a method for the treatment and/or care of those conditions, disorders and/or diseases of mammals, preferably humans, which are improved or prevented by heat shock protein synthesis stimulation, preferably Hsp70; which comprises administering an effective amount of at least one peptide of general formula (I), its stereoisomers, mixtures thereof and/or its cosmetically or pharmaceutically acceptable salts, preferably in the form of a cosmetic or a pharmaceutical composition containing them.

In a preferred embodiment, the conditions, disorders and/or pathologies which are improved or prevented by heat shock protein synthesis stimulation are selected from a group formed by epidermolysis bullosa and alopecia, including alopecia caused by chemotherapy treatment for cancer.

Another additional aspect of this invention relates to a method for the treatment and/or care of the skin, mucous membranes and/or hair which reduces, delays, and/or prevents cell damage induced by UV radiation, thermal stress, oxidative stress, osmotic shock, inflammation, hypoxia, exposure to pollutants, lack of nourishment and lack of hydration; which comprises administering an effective amount of at least one peptide of general formula (I), its stereoisomers, mixtures thereof and/or its cosmetically or pharmaceutically acceptable salts, preferably in the form of a cosmetic or a pharmaceutical composition containing them.

According to an additional aspect, this invention relates to the treatment and/or care which reduces, delays and/or prevents the signs of aging and/or photoaging, which comprises administering an effective amount of at least one peptide of general formula (I), its stereoisomers, mixtures thereof and/or its cosmetically or pharmaceutically acceptable salts, preferably in the form of a cosmetic or a pharmaceutical composition containing them.

Another additional aspect of this invention relates to a method for the treatment and/or care of the skin and/or mucous membranes which stimulates healing and/or re-epithelialization of wounds, preferably wounds that are a consequence of diabetes, and which comprises administering an effective amount of at least one peptide of general formula (I), its stereoisomers, mixtures thereof and/or its cosmetically or pharmaceutically acceptable salts, preferably in the form of a cosmetic or a pharmaceutical composition containing them.

Another additional aspect of this invention relates to a method for the treatment and/or care of the skin and/or hair which delays and/or prevents hair loss or induces hair growth, which comprises administering an effective amount of at least one peptide of general formula (I), its stereoisomers, mixtures thereof and/or its cosmetically or pharmaceutically acceptable salts, preferably in the form of a cosmetic or a pharmaceutical composition containing them.

In a more particular aspect, the treatment and/or care of this invention is performed by topical or transdermal application; preferably, the topical or transdermal application is performed via iontophoresis, sonophoresis, electroporation, mechanical pressure, osmotic pressure gradient, occlusive cure, microinjections, needle-free injections by means of pressure, by means of micro-electric patches or any combination thereof.

In another particular aspect, the treatment and/or care is performed by oral administration.

In another particular aspect, the treatment and/or care is performed by parenteral application.

The frequency of application or administration can vary greatly, depending on the needs of each subject and the severity of the condition, disorder or disease to be treated or cared for, with a recommendation of an application or administration range from once a month to ten times a day, preferably from once a week to four times a day, more preferably from three times a week to three times a day, even more preferably once or twice a day.

The following specific examples provided here illustrate the nature of this invention. These examples are included for illustrative purposes only and should not be construed as limitations on the invention claimed herein.

EXAMPLES

General Methodology

All reagents and solvents are of synthesis quality and are used without additional treatment.

Abbreviations

The abbreviations used for amino acids follow the IUPAC-IUB Joint Commission on Biochemical Nomenclature rules outlined in *Eur. J. Biochem.* (1984) 138:9-37 and in *J. Biol. Chem.* (1989) 264:633-673.

®, resin; Ac, acetyl; DNA, deoxyribonucleic acid; Adpoc, 1-(1-adamantyl)-1-methylethoxy-carbonyl; All, allyl; Alloc, allyloxycarbonyl; AM, 2-[4-aminomethyl-(2,4-dimethoxyphenyl)]phenoxyacetic acid; Arg, arginine; Asn, asparagine, Boc, tert-butyloxycarbonyl; 2-BrZ, 2-bromobenzyloxycarbonyl; Bzl, benzyl; Cbz, carboxybenzyl; cHx, cyclohexyl; ClTrt-®, 2-chlorotrityl resin; ClZ, 2-chlorobenzyl; cps, centipoise; C-terminal, carboxy-terminal; DCM, dichloromethane; Dde, N-[1-(4,4-dimethyl-2,6-dioxocyclohex-1-ylidene)ethyl; 2,6-diClZ, 2,6-dichlorobenzyl; DIEA, N,N-diisopropylethylamine; DIPCDI, N,N'-diisopropylcarbodiimide; Dmab, 4-(N-[1-(4,4-dimethyl-2,6-dioxocyclohexylidene)-3-methylbutyl]amino)benzyl; DMEM, Dulbecco's Modified Eagle Medium; DMF, N,N-dimethylformamide; DMSO, dimethyl sulfoxide; Dnp, 2,4-dinitrophenol; DPPC, dipalmitoylphosphatidylcholine; EDTA, ethylenediaminetetraacetic acid; ELISA, enzyme-linked immunoabsorption assay; equiv, equivalent; ESI-MS, electrospray ionization mass spectrometry; Fm, fluorenylmethyl; Fmoc, 9-fluorenylmethyloxycarbonyl; Gln, glutamine; grp, glucose-regulated proteins, His, histidine; HOAt, 1-hydroxy-7-azabenzotriazole; HOBt, 1-hydroxybenzotriazole; HPLC, high performance liquid chromatography; Hsp, heat shock proteins; INCI, International Nomenclature of Cosmetic Ingredients; ivDde, 1-(4,4-dimethyl-2,6-dioxocyclohexylidene)-3-methyl-butyl; kDa, kiloDalton; Leu, leucine; MBHA, p-methylbenzhydrylamine; MeCN, acetonitrile; MeOH, methanol; MLV, multilaminar vesicles; MPD, minimal pigmenting dose; Mtt, methoxytrityl or methyltrityl; MTT, 3-(4,5-dimethylthiazol-2-yl)-2,5-diphenyltetrazolium bromide; N-terminal, amino-terminal; PAL, 5-(4-aminomethyl-3,5-dimethoxyphenoxy)valeric acid; Palm, palmitoyl; PBS, phosphate buffer saline; pNZ, p-nitrobenzyloxycarbonyl; Pro, proline; rpm, revolutions per minute; qs, quantity sufficient; q.s.p., quantity sufficient for; tBu, tert-butyl; Teoc, 2-(trimethylsilyl)ethyloxycarbonyl; TFA, trifluoroacetic acid; THF, tetrahydrofuran; TIS, triisopropylsilane; Troc, 2,2,2-trichloroethyloxycarbonyl; Trt, triphenylmethyl or trityl; Trt, trityl; Tyr, tyrosine; ULV, unilaminar vesicles; UV, ultra-violeta; Z, benzyloxycarbonyl.

Chemical Synthesis

All synthetic processes were carried out in polypropylene syringes fitted with porous polyethylene discs or Pyrex® reactors fitted with porous plates. The solvents and soluble reagents were removed by suction. The Fmoc group was removed with piperidine-DMF (2:8, v/v) (1×1 min, 1×5 min, 5 mL/g resin) [Lloyd-Williams P., Albericio F. and Giralt E. (1997) "*Chemical Approaches to the Synthesis of Peptides and Proteins*" CRC, Boca Raton, Fla., USA]. Washes between stages of deprotection, coupling, and, again, deprotection, were carried out with DMF (3×1 min) each time using 10 mL solvent/g resin. Coupling reactions were performed with 3 mL solvent/g resin. The control of the couplings was performed by carrying out the ninhydrin test [Kaiser E., Colescott R. L., Bossinger C. D. and Cook P. I. (1970) "*Color test for detection of free terminal amino groups in the solid-phase synthesis of peptides*" Anal. Biochem. 34:595-598] or chloranil test [Christensen T. (1979) "*A qualitative test for monitoring coupling completeness in solid-phase peptide synthesis using chloranil*" Acta Chem. Scand. 33B:763-766]. All synthetic reactions and washes were carried out at room temperature.

HPLC chromatographic analysis was carried out with Shimadzu equipment (Kyoto, Japan) using a reversed-phase column thermostatized at 30° C. (250×4.0 mm, Kromasil C$_8$, 5 μm, Akzo Nobel, Sweden). The elution was carried out using a gradient of acetonitrile (+0.07% TFA) in water (+0.1% TFA) at a flow rate of 1 mL/min and detection was carried out at 220 nm.

Example 1

Obtaining Fmoc-W$_n$—X$_m$-AA$_1$-AA$_2$-AA$_3$-AA$_4$-Y$_p$—Z$_q$—O-2-ClTrt-®, wherein AA$_1$ is -L-His-; AA$_2$ is -L-His-, -L-Leu- or -L-Pro-; AA$_3$ is -L-Leu-; AA$_4$ is -L-Arg- or -L-Asn-; and n, m, p and q are 0

5.71 g of Fmoc-L-Arg(Pbf)-OH or 5.25 g of Fmoc-L-Asn (Trt)-OH (8.8 mmol; 1 equiv) dissolved in 55 mL of DCM to which was added 1.3 mL of DIEA (7.6 mmol; 0.86 equiv) were coupled onto the dry 2-chlorotrityl resin (5.5 g; 8.8 mmol). They were stirred for 5 min, after which 2.5 mL of DIEA were added (14.6 mmol; 1.66 equiv). The mixture was allowed to react for 40 min. Remaining chloride groups were blocked by treatment with 4.4 mL of MeOH.

The N-terminal Fmoc group was deprotected as described in the general methods and 7.77 g of Fmoc-L-Leu-OH (22 mmol; 2.5 equiv) were coupled onto the peptidyl resin in the presence of DIPCDI (3.39 mL, 22 mmol, 2.5 equiv) and HOBt (3.37 g, 22 mmol, 2.5 equiv) using DMF as a solvent for 1 hour. The resin was then washed as described in the general methods and the deprotection treatment of the Fmoc group was repeated to couple the next amino acid. Following the protocols described 13.63 g of Fmoc-L-His(Trt)-OH, 7.77 g of Fmoc-L-Leu-OH or 7.42 g of Fmoc-L-Pro-OH (22 mmol; 2.5 equiv) were sequentially coupled; and subsequently 13.63 g of Fmoc-L-His(Trt)-OH (22 mmol; 2.5 equiv) each coupling in the presence of 3.37 g of HOBt (22 mmol; 2.5 equiv) and 3.39 mL of DIPCDI (22 mmol; 2.5 equiv).

After the synthesis, the peptidyl resins were washed with DCM (5×3 min) and dried by nitrogen stream.

Example 2

Prophetic

Obtaining Fmoc-W$_n$—X$_m$-AA$_1$-AA$_2$-AA$_3$-AA$_4$-Y$_p$—Z$_q$-AM-MBHA-®, Wherein AA$_1$ is -L-His-; AA$_2$ is -L-His-, -L-Leu- or -L-Pro-; AA$_3$ is -L-Leu-; AA$_4$ is -L-Arg- or -L-Asn-; and n, m, p and q are 0

6.85 g of the Fmoc-AM-MBHA resin with a functionalization of 0.73 mmol/g (5 mmol) was treated with piperidine-DMF according to the described general protocol in order to remove the Fmoc group. 16.22 g of Fmoc-L-Arg(Pbf)-OH or 14.92 g de Fmoc-L-Asn(Trt)-OH (25 mmol; 5 equiv) were incorporated onto the deprotected resin in the presence of DIPCDI (3.85 mL; 25 mmol; 5 equiv) and HOBt (3.85 g; 25 mmol; 5 equiv) using DMF as a solvent for 1 hour.

The resin was then washed as described in the general methods and the deprotection treatment of the Fmoc group was repeated to couple the next amino acid. Following the previously described protocols 8.84 g of Fmoc-L-Leu-OH (25 mmol; 5 equiv); 15.49 g of Fmoc-L-His(Trt)-OH, 8.84 g of Fmoc-L-Leu-OH or 8.44 g of Fmoc-L-Pro-OH (25 mmol; 5 equiv); and subsequently 15.49 g of Fmoc-L-His(Trt)-OH (25 mmol; 5 equiv) were coupled sequentially each coupling in the presence of 3.85 g of HOBt (25 mmol; 5 equiv) and 3.85 mL of DIPCDI (25 mmol; 5 equiv).

After the synthesis, the peptidyl resins were washed with DCM (5×3 min) and dried by nitrogen stream.

Example 3

General Process for Removal of Fmoc N-Terminal Protective Group

The N-terminal Fmoc group of the peptidyl resins obtained in Examples 1 was deprotected as described in the general methods (20% piperidine in DMF, 1×5 min+1×20 min). The peptidyl resins were washed with DMF (5×1 min), DCM (4×1 min), diethyl ether (4×1 min) and dried under vacuum. The same process could have been applied to the N-terminal Fmoc group of the peptidyl resin obtained in prophetic Example 2.

Example 4

Prophetic

Process for Introducing the $R_1$ Palmitoyl Group onto the Peptidyl Resins Obtained in Example 3

2.56 g of palmitic acid (10 mmol; 10 equiv) pre-dissolved in DMF (1 mL) were added onto 1 mmol of the peptidyl resins obtained in Example 3, in the presence of 1.53 g of HOBt (10 mmol; 10 equiv) and 1.54 mL of DIPCDI (10 mmol; 10 equiv). They were allowed to react for 15 hours, after which the resins were washed with THF (5×1 min), DCM (5×1 min), DMF (5×1 min), MeOH (5×1 min), DMF (5×1 min) THF (5×1 min), DMF (5×1 min), DCM (4×1 min), ether (3×1 min), and were dried under vacuum.

Example 5

Process for Introducing the $R_1$ Acetyl Group onto the Peptidyl Resins Obtained in Example 3

1 mmol of the peptidyl resins obtained in Example 3 was treated with 25 equiv of acetic anhydride in the presence of 25 equiv of DIEA using 5 mL of DMF as a solvent. They were allowed to react for 30 mins, after which the peptidyl resins was washed with DMF (5×1 min), DCM (4×1 min), diethyl ether (4×1 min) and dried under vacuum.

Example 6

Cleavage Process from the Polymeric Support of the Peptidyl Resins Obtained in Examples 3, 4 and 5

200 mg of the dried peptidyl resins obtained in Example 5 were treated with 5 mL of TFA:TIS:$H_2O$ (90:5:5) for 2 hours at room temperature under stirring. The filtrates was collected onto 50 mL cold diethyl ether, filtered through a polypropylene syringes fitted with a porous polyethylene discs and washed 5 times with 50 mL diethyl ether. The final precipitates was dried under vacuum.

HPLC analysis of the obtained peptides in gradients of MeCN (+0.07% TFA) in $H_2O$ (+0.1% TFA) showed a purity exceeding 80%. The identity of the peptides obtained was confirmed by ESI-MS. The same procedures could have been applied to the peptidyl resins obtained in Examples 3 and 4.

Example 7

(Prophetic)

Cleavage Process of the Polymeric Support and Functionalization with Substituted $R_2$ Amine Obtaining Ac-$W_n$—$X_m$-$AA_1$-$AA_2$-$AA_3$-$AA_4$-$Y_p$—$Z_q$—NH—$(CH_2)_{15}$—$CH_3$, Wherein $AA_1$ is -L-His-; $AA_2$ is -L-His-, -L-Leu- or -L-Pro-; $AA_3$ is -L-Leu-; $AA_4$ is -L-Arg- or -L-Asn-; and n, m, p and q are 0.

The peptides Ac-$W_n$—$X_m$-$AA_1$-$AA_2$-$AA_3$-$AA_4$-$Y_p$—$Z_q$—OH with fully protected side chains were obtained by treating 150 mg of the peptidyl resins Ac-$W_n$—$X_m$-$AA_1$-$AA_2$-$AA_3$-$AA_4$-$Y_p$—$Z_q$—O-2-ClTrt-® of Example 5, previously desiccated under vacuum in the presence of KOH, with 3 mL of a 3% solution of TFA in DCM for 5 min. The filtrates were collected onto 50 mL of cold diethyl ether and the treatment was repeated three times. The ethereal solutions were evaporated to dryness at reduced pressure and room temperature, the precipitates were redissolved in 50% MeCN in $H_2O$ and lyophilized.

10 mg of the obtained crude peptides were weighed in a flask and 3 equiv of hexadecylamine and 25 mL of anhydrous DMF were added. 2 equiv of DIPCDI were added, and left to react under magnetic stirring at 47° C. The reactions were monitored by HPLC until disappearance of the initial products, which were complete after 24-48 hours. Solvents were evaporated to dryness and co-evaporated twice with DCM. The obtained residues [Ac-$W_n$—$X_m$-$AA_1$-$AA_2$-$AA_3$-$AA_4$-$Y_p$—$Z_q$—NH—$(CH_2)_{15}$—$CH_3$ with fully protected side chains] were redissolved in 25 mL of a mixture of TFA-DCM-anisole (49:49:2) and left to react for 30 min at room temperature. 250 mL of cold diethyl ether was added, the solvents were evaporated under reduced pressure and two additional co-evaporations with ether were carried out. The residues were dissolved in a mixture of 50% MeCN in $H_2O$ and lyophilized.

HPLC analysis of the obtained peptides in gradients of MeCN (+0.07% TFA) in $H_2O$ (+0.1% TFA) showed a purity exceeding 65% in all cases. The identity of the peptides obtained was confirmed by ESI-MS.

Example 8

Hsp70 Synthesis Stimulation Assay

Hsp70 synthesis stimulation was assessed in a human keratinocyte cell line in the presence of the peptides of the invention. The cells were seeded ($10^6$ cells/6-well plate) and incubated for 24 hours in DMEM, after which the peptides were added to 200 μM in culture medium and were incubated for another 16-24 hours. The proteasome inhibitor MG-132 at 10 μM was used as a positive control and vehicle (culture medium) as a negative control. After the incubation period, the cells were washed with PBS, lysed and centrifuged at 12,000 rpm at 4° C. for 10 min. The supernatants were collected, and the Hsp70 levels were determined by carrying out a competitive ELISA assay following the protocols of the commercial kit (DuoSet IC human/mouse total HSP70 ELISA kit, R&D Systems Inc.)

Table 2 provides details of the peptides which showed Hsp70 stimulation level values greater than 15%. Hsp70 levels were normalized with regards to the average basal values.

TABLE 2

Increase in Hsp70 levels

| Treatment | Hsp70 increase |
| --- | --- |
| Vehicle | 0% |
| MG-132 | 294% |
| Ac-L-His-L-Leu-L-Leu-L-Arg-OH | 28% |
| Ac-L-His-L-Pro-L-Leu-L-Arg-OH | 42% |

Example 9

Assay of Photoprotective Efficiency of Ac-L-His-L-Pro-L-Leu-L-Arg-OH and Ac-L-His-L-Leu-L-Leu-L-Arg-OH in Human Keratinocyte Cultures The human keratinocytes were maintained in culture for 24 hours in 96-well plates for monolayer formation and the cells were pre-incubated in darkness with 0.1 mM of Ac-L-His-L-Pro-L-Leu-L-Arg-OH, Ac-L-His-L-Leu-L-Leu-L-Arg-OH in culture medium or with vehicle (culture medium) for 2 hours at 37° C. Subsequently the cells were radiated with UVB at an energy of 800 J/m$^2$. A control plate with vehicle was maintained in the dark without radiation for the same time at room temperature. After the irradiation period the cells' medium was replaced by a fresh medium and the cells were incubated for additional 24 hours. Cell viability was determined by the MTT method, adding 5 mg/mL of the MTT solution to each well and incubating the plate for 4 hours at 37° C., after which time the medium was removed, 100μL of DMSO was added and the plate was stirred at room temperature for 15 min. The optical density of each well was measured at 570 nm in a spectrophotometer.

TABLE 3

Photoprotective efficiency of the peptides of the invention

| TREATMENT | CELL VIABILITY | PHOTO-PROTECTIVE EFFICIENCY |
| --- | --- | --- |
| Non-irradiated vehicle | 100.0% | — |
| Ac-L-His-L-Pro-L-Leu-L-Arg-OH | 97.2% | |
| Ac-L-His-L-Leu-L-Leu-L-Arg-OH | 87.7% | |

Example 10

Prophetic

Preparation of a Cosmetic Composition Containing Palm-L-His-L-Pro-L-Leu-L-Asn-NH$_2$

| | INGREDIENT (INCI Nomenclature) | % IN WEIGHT |
| --- | --- | --- |
| A | WATER (AQUA) | q.s.p. 100 |
| | PRESERVATIVES | 0.45 |
| | IMIDAZOLIDINYL UREA | 0.095 |
| | DISODIUM EDTA | 0.14 |
| | GLYCERIN | 4.75 |
| | PROPYLENE GLYCOL | 2.85 |
| B | WATER (AQUA), POLYACRYLAMIDE, C13-14 ISOPARAFFIN, LAURETH-7 | 2.85 |
| | ETHYLHEXYL COCOATE | 4.75 |
| | CAPRYLIC/CAPRIC TRIGLYCERIDE | 4.75 |
| C | DIMETHICONE | 1.9 |

| | INGREDIENT (INCI Nomenclature) | % IN WEIGHT |
| --- | --- | --- |
| D | TRIETHANOLAMINE | q.s. |
| E | FRAGRANCE (PARFUM) | 0.19 |
| F | Palm-L-His-L-Pro-L-Leu-L-Asn-NH$_2$ 0,01%, BUTYLENGLYCOL, ALCOHOL DENAT | 5 |

Phase A was dissolved in an appropriate reactor. In another reactor, phase B was mixed, formed by Sepigel® 305 [INCI: Aqua (Water), Polyacrylamide, C13-C14 Isoparaffin, Laureth-7], Myritol® 308 [INCI: Caprylic/Capric Triglyceride] and ethylhexyl cocoate and once homogenized it was slowly added onto phase A under stirring. Then phase C was added under stirring, and subsequently phase F was added at 35° C. The pH was adjusted to 5.5-7.0 with phase D and phase E was added.

Example 11

Prophetic

Preparation of Liposomes Containing Ac-L-His-L-Leu-L-Leu-L-Arg-OH

| INGREDIENT (INCI Nomenclature) | % IN WEIGHT |
| --- | --- |
| PHOSPHATIDYLCHOLINE | 4.0 |
| Ac-L-His-L-Leu-L-Leu-L-Arg-OH | 0.2 |
| PRESERVATIVES | 0.50 |
| AQUA (WATER) | q.s.p. 100 |

Dipalmitoylphosphatidylcholine (DPPC) was weighed and dissolved in chloroform. The solvent was evaporated under vacuum until obtaining a fine phospholipid layer, and this layer was hydrated under treatment at 55° C. with an aqueous solution of the peptide at the desired concentration (containing Phenonip®), and MLV liposomes were obtained. ULV liposomes were obtained by submerging the MLV liposomes in an ultrasound bath at 55° C. for 8 cycles of 2 mins at intervals of 5 mins. The size of the ULV liposomes was reduced by passing them through a high pressure extrusion system.

Example 12

Prophetic

Preparation of a Composition in the Form of a Liposome Gel Containing Ac-L-His-L-Leu-L-Leu-L-Arg-OH The liposomes of Example 11 were dispersed in water with the preservatives (EDTA, imidazolidinyl urea and Phenonip®) under light stirring. Hispagel® 200 was added [INCI: Aqua (Water), glycerin, glyceryl polyacrylate] and was lightly stirred until a homogenous mixture was obtained.

| INGREDIENT (INCI Nomenclature) | % IN WEIGHT |
| --- | --- |
| LIPOSOMES CONTAINING Ac-L-His-L-Leu-L-Leu-L-Arg-OH (1%) | 10.00 |
| DISODIUM EDTA | 0.15 |
| IMIDAZOLIDINYL UREA | 0.10 |
| PRESERVATIVE | 0.50 |

-continued

| INGREDIENT (INCI Nomenclature) | % IN WEIGHT |
|---|---|
| AQUA (WATER) | 29.25 |
| AQUA (WATER), GLYCERIN, GLYCERYL POLYACRYLATE | 60.00 |

Example 13

Prophetic

Composition of a Facial Cream Containing Ac-L-His-L-Pro-L-Leu-L-Arg-OH

| | INGREDIENT (INCI Nomenclature) | % IN WEIGHT |
|---|---|---|
| A | BUTYROSPERMUM PARKII | 3.5-4.5 |
|   | CETEARYL ETHYLHEXANOATE | 3-5 |
|   | GLYCERYL STEARATE S.E. | 1.5-2.5 |
|   | SQUALANE | 0.5-1 |
|   | PEG-100 STEARATE | 1 |
|   | POLYSORBATE 60 | 0.30 |
|   | CETYL PALMITATE | 1.5-2.5 |
|   | DIMETHICONE | 2.5-3.5 |
|   | CETEARYL ALCOHOL | 1.5-2.5 |
|   | PALMITIC ACID | 0.5 |
| B | AQUA (WATER) | 2 |
|   | GLYCERIN | 1.5-2.5 |
|   | BUTYLENE GLYCOL | 1-3 |
|   | MANNITOL | 0.5-1.5 |
|   | HYDROGENATED LECITHIN | 0.5-1.5 |
|   | PROPYLENE GLYCOL | 0.5-1.5 |
| C | CARBOMER | 0.4 |
|   | ETHYLHEXYL PALMITATE | 1.5-2.5 |
| D | TROMETHAMINE | 0.4 |
|   | AQUA (WATER) | 1 |
| E | PRESERVATIVES | q.s. |
| F | Ac-L-His-L-Pro-L-Leu-L-Arg-OH | 0.001 |
|   | AQUA (WATER) | q.s.p. 100 |

Preparation

Mix the components of Phase A and heat to 70° C.

Mix the components of Phase B and heat to 70° C.

Add Phase C to Phase B stirring with the homogenizer (Silverson) for 5 minutes.

Add Phase A little by little to the mixture of phases B and C with a homogenizer and maintain homogenization for 15 minutes.

Start the cooling until 30-35° C. under light stirring. At 50° C. add Phase D. Keep stirring. At 35-38° C. add Phases E and F which have been previously solubilized.

Example 14

Prophetic

Preparation of a Composition of Mixed Micelles Containing Ac-L-His-L-Leu-L-Leu-L-Arg-OH The ingredients of phase A were weighed in a vessel suitable for the whole sample and warmed slightly to about 30° C. to help to dissolve some of the preservatives. Next, phase B components were added and homogenized under moderate stirring.

Phase C was then added under continuous stirring, after which phase D (Oramix® CG 110 [INCI: Aqua (Water), Caprilyl/Capryl Glucoside]) was added with slow stirring to avoid foaming.

The pH was adjusted to 5.5-6.5.

| | INGREDIENT (INCI Nomenclature) | % IN WEIGHT |
|---|---|---|
| A | AQUA (WATER) | q.s.p. 100 |
|   | PHENOXYETHANOL | 0.5 |
|   | CAPRILYL GLYCOL | 0.5 |
|   | POTASIUM SORBATE | 0.3 |
| B | AQUA (WATER) | 27.5 |
|   | Ac-L-His-L-Leu-L-Leu-L-Arg-OH | 0.025 |
|   | LECITHIN | 4.0 |
| C | XANTHAN GUM | 0.4 |
| D | AQUA (WATER), CAPRILYL/CAPRYL GLUCOSIDE | 30 |

Example 15

Prophetic

Microemulsion Composition Containing Palm-L-His-L-Pro-L-Leu-L-Asn-NH$_2$

The ingredients of phase B were weighed in a vessel suitable for the complete sample. Next, phase D was added to phase B and homogenized under continuous stirring. Phase A was then added to the mixture. Lastly, phase C was added.

| | INGREDIENT (INCI Nomenclature) | % IN WEIGHT |
|---|---|---|
| A | DIETHYLHEXYL SODIUM SULFOSUCCINATE | 1.35 |
|   | ISOSTEARIC ACID | 7.65 |
| B | AQUA (WATER) | 0.2 |
|   | ALCOHOL DENAT | 0.8 |
| C | ETHYLHEXYL COCOATE | q.s.p. 100 |
| D | Palm-L-His-L-Pro-L-Leu-L-Asn-NH$_2$ | 0.005 |

Example 16

Prophetic

Composition of a Capillary Lotion Containing Ac-L-His-L-Leu-L-Leu-L-Arg-OH

Mix the components of Phase A slowly under stirring. Slowly add Phase B to Phase A under stirring until homogenization is complete.

| | INGREDIENT (INCI Nomenclature) | % IN WEIGHT |
|---|---|---|
| A | ALCOHOL DENAT. | 50-60 |
|   | PANTHENOL | 0.05-0.15 |
|   | ZINC RICINOLEATE | 0.05-0.10 |
|   | FRAGRANCE | 0.02 |
|   | Ac-L-His-L-Leu-L-Leu-L-Arg-OH | 0.01 |
| B | AQUA (WATER) | q.s.p. 100 |

The invention claimed is:
1. A peptide of general formula (I)

$$R_1—W_n—X_m-AA_1-AA_2-AA_3-AA_4-Y_p—Z_q—R_2 \quad (I)$$

its stereoisomers, mixtures thereof and/or its cosmetically or pharmaceutically acceptable salts, wherein:
AA$_1$ is -His-;
AA$_2$ is selected from the group consisting of -His-, -Leu- and -Pro-;
AA$_3$ is -Leu-;
AA$_4$ is selected from the group consisting of -Arg- and -Asn-;
W, X, Y and Z are independently selected from amongst themselves from the group consisting of the codified amino acids and uncodified amino acids;
n, m, p and q are independently selected from amongst themselves and have a value between 0 and 1;
n+m+p+q is less or equal to 2;
R$_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO— wherein R$_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;
R$_2$ is selected from the group consisting of —NR$_3$R$_4$, —OR$_3$ and —SR$_3$, wherein R$_3$ and R$_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl;
with the proviso that when AA$_2$ is -Leu-, AA$_4$ is -Asn- and Y is -Gln- then Z is not -Leu-;
and with the proviso that when AA$_2$ is -His-, AA$_4$ is -Arg- and Y or Z are -Tyr- then p+q is not 1,
wherein when R$_1$ or R$_5$ is a substituted non-cyclic aliphatic group or substituted aralkyl group, each substituent of said substituted non-cyclic aliphatic group or substituted aralkyl group is selected from the group consisting of hydroxyl, C$_1$-C$_4$ alcoxyl, C$_1$-C$_4$ oxycarbonyl, halogen, cyano, nitro, azido, C$_1$-C$_4$ alkylsulfonyl, thiol, C$_1$-C$_4$ alkylthio, aryloxyl, and —NR$_b$(C=NR$_b$)NR$_b$R$_c$, where R$_b$ and R$_c$ are independently selected from the group consisting of H, C$_1$-C$_4$ alkyl, C$_2$-C$_4$ alkenyl_C$_2$-C$_4$ alkynyl_C$_3$-C$_{10}$ cycloalkyl, C$_6$-C$_{18}$ aryl, C$_7$-C$_{17}$ aralkyl, and 3-10-membered-heterocyclyl, and
wherein when R$_3$ or R$_4$ is a substituted non-cyclic aliphatic group, substituted heterocyclyl group, substituted heteroarylalkyl group, or substituted aralkyl group, each substituent of said substituted non-cyclic aliphatic group, substituted heterocyclyl group, substituted heteroarylalkyl group, or substituted aralkyl group is selected from the group consisting of hydroxyl, C$_1$-C$_4$ alcoxyl, amino, C$_1$-C$_4$ aminoalkyl, C$_1$-C$_4$ carbonyloxyl, halogen, cyano, nitro, azido, C$_1$-C$_4$ alkylsulfonyl, thiol, C$_1$C$_4$ alkythio, aryloxyl, and —NR$_b$(C=NR$_b$)NR$_b$R$_c$, where R$_b$ and R$_c$ are independently selected from the group consisting of H, C$_1$-C$_4$ alkyl, C$_2$-C$_4$ alkenyl, C$_2$-C$_4$ alkynyl, C$_3$-C$_{10}$ cycloalkyl, C$_6$-C$_{18}$ aryl, C$_7$-C$_{17}$ aralkyl 3-10-membered-heterocyclyl.

2. The peptide according to claim 1, wherein R$_1$ is selected from the group consisting of H and R$_5$—CO—, wherein R$_5$ is selected from the group consisting of substituted or unsubstituted alkyl C$_1$-C$_{24}$, substituted or unsubstituted alkenyl C$_2$-C$_{24}$, substituted or unsubstituted alkynyl C$_2$-C$_{24}$, substituted or unsubstituted cycloalkyl C$_3$-C$_{24}$, substituted or unsubstituted cycloalkenyl C$_5$-C$_{24}$, substituted or unsubstituted cycloalkynyl C$_5$-C$_{24}$, substituted or unsubstituted aryl C$_6$-C$_{30}$, substituted or unsubstituted aralkyl C$_7$-C$_{24}$, substituted or unsubstituted heterocycyl with 3-10 ring members, and substituted or unsubstituted heteroarylalkyl of 2 to 24 carbon atoms and 1 to 3 atoms other than carbon and an alkyl chain of 1 to 6 carbon atoms.

3. The peptide according to claim 1, wherein R$_1$ is selected from the group consisting of H, acetyl, tert-butanoyl, hexanoyl, 2-methylhexanoyl, cyclohexancarboxyl, octanoyl, decanoyl, lauroyl, myristoyl, palmitoyl, stearoyl, oleoyl and linoleoyl.

4. The peptide according to claim 1, wherein R$_2$ is —NR$_3$R$_4$ or —OR$_3$, wherein R$_3$ and R$_4$ are independently selected from the group consisting of H, substituted or unsubstituted alkyl C$_1$-C$_{24}$, substituted or unsubstituted alkenyl C$_2$-C$_{24}$, substituted or unsubstituted alkynyl C$_2$-C$_{24}$, substituted or unsubstituted cycloalkyl C$_3$-C$_{24}$, substituted or unsubstituted cycloalkenyl C$_5$-C$_{24}$, substituted or unsubstituted cycloalkynyl C$_8$-C$_{24}$, substituted or unsubstituted aryl C$_6$-C$_{30}$, substituted or unsubstituted aralkyl C$_7$-C$_{24}$, substituted or unsubstituted heterocycyl with 3-10 ring members, and substituted or unsubstituted heteroarylalkyl of 2 to 24 carbon atoms and 1 to 3 atoms other than carbon and an alkyl chain of 1 to 6 carbon atoms.

5. The peptide according to claim 4, wherein R$_3$ and R$_4$ are independently selected from the group consisting of H, methyl, ethyl, hexyl, dodecyl and hexadecyl.

6. The peptide according to claim 1, wherein R$_1$ is selected from the group consisting of H, acetyl, lauroyl, myristoyl and palmitoyl, AA$_2$ is -L-Leu-, AA$_4$ is -L-Arg-, and R$_2$ is —NR$_3$R$_4$ or —OR$_3$ wherein R$_3$ and R$_4$ are independently selected from H, methyl, ethyl, hexyl, dodecyl and hexadecyl.

7. The peptide according to claim 1, wherein R$_1$ is selected from the group consisting of H, acetyl, lauroyl, myristoyl and palmitoyl, AA$_2$ is -L-Pro-, AA$_4$ is -L-Arg-, and R$_2$ is —NR$_3$R$_4$ or —OR$_3$ wherein R$_3$ and R$_4$ are independently selected from H, methyl, ethyl, hexyl, dodecyl and hexadecyl.

8. A process for preparation of a peptide comprising synthesizing a peptide of general formula (I), its stereoisomers, mixtures thereof and/or its cosmetically or pharmaceutically acceptable salts, according to claim 1, the synthesis including sequential coupling of at least one of amino acids and peptides, wherein the coupling is carried out on solid phase or in solution.

9. A cosmetic or pharmaceutical composition which comprises a cosmetically or pharmaceutically effective amount of at least one peptide of general formula (I), its stereoisomers, mixtures thereof and/or its cosmetically or pharmaceutically acceptable salts, according to claim 1, and at least one cosmetically or pharmaceutically acceptable excipient or adjuvant.

10. A composition according to claim 9, wherein the peptide of general formula (I), its stereoisomers, mixtures thereof and/or its cosmetically or pharmaceutically acceptable salts, is found in a concentration between 0.000001% and 20% in weight, with regards to the total weight of the composition.

11. A composition according to claim 9, wherein the peptide of general formula (I), its stereoisomers, mixtures thereof and/or its cosmetically or pharmaceutically acceptable salts, is incorporated into a cosmetic or pharmaceutical delivery system or sustained release system selected from the group consisting of liposomes, mixed liposomes, oleosomes, niosomes, ethosomes, millicapsules, microcapsules, nanocapsules, sponges, cyclodextrins, vesicles, micelles, mixed micelles of surfactants, surfactant-phospholipid mixed micelles, millispheres, microspheres, nanospheres, liposheres, microemulsions, nanoemulsiones, miniparticles, milliparticles, microparticles, nanoparticles, solid lipid nanoparticles and nanostructured lipid carriers or is found adsorbed on a solid organic polymer or solid mineral support selected from the group consisting of talc, bentonite, silica, starch and maltodextrin.

12. A composition according to claim 9, wherein said composition is presented in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, ointments, mousses, pomades, powders, bars, pencils, sprays, aerosols, capsules, gelatin capsules, soft capsules, hard capsules, tablets, sugar coated tablets, granules, chewing gum, solutions, suspensions, emulsions, syrups, polysaccharide films, jellies and gelatins.

13. A composition according to claim 9, wherein said composition is found incorporated into a product selected from the group consisting of under-eye concealers, make-up foundation, make-up removing lotions, make-up removing milks, eye shadows, lipsticks, lip gloss, lip protectors and powders.

14. A composition according to claim 9, wherein the peptide of general formula (I), its stereoisomers, mixtures thereof and/or its cosmetically or pharmaceutically acceptable salts, is incorporated into a fabric, a non-woven fabric or a medical device.

15. A composition according to claim 9, wherein said composition further comprises a cosmetically or pharmaceutically effective amount of at least one adjuvant selected from the group comprised of heat shock proteins, other heat shock protein synthesis stimulating agents, acetylcholine-receptor aggregation inhibitors, muscle contraction inhibiting agents, anticholinergic agents, elastase inhibiting agents, matrix metalloproteinase inhibiting agents, melanin synthesis stimulating or inhibiting agents, whitening or depigmenting agents, propigmenting agents, self-tanning agents, anti-aging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl specie scavengers, anti-glycation agents, antihistamine agents, antiviral agents, antiparasitic agents, emulsifiers, emollients, organic solvents, liquid propellants, skin conditioners, humectants, substances that retain moisture, alpha hydroxyacids, beta hydroxyacids, moisturizers, epidermal hydrolytic enzymes, vitamins, amino acids, proteins, pigments or colorants, dyes, gelling polymers, thickeners, surfactants, softening agents, anti-wrinkle agents, agents able to reduce or treat bags under the eyes, exfoliating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, aquaporin synthesis-stimulating agents, hyaluronic acid synthesis-stimulating agents, fibronectin synthesis-stimulating agents, sirtuin synthesis-stimulating agents, agents stimulating the synthesis of lipids and components of the stratum corneum, ceramides, fatty acids, agents that inhibit collagen degradation, agents that inhibit elastin degradation, agents that inhibit serine proteases such as cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating adipocyte differentiation, agents that inhibit acetylcholinesterase, skin relaxant agents, glycosaminoglycan synthesis-stimulating agents, antihyperkeratosis agents, comedolytic agents, antipsoriasis agents, DNA repair agents, DNA protecting agents, stabilizers, anti-itching agents, agents for the treatment and/or care of sensitive skin, firming agents, anti-stretch mark agents, binding agents, agents regulating sebum production, lipolytic agents or agents stimulating lipolysis, anti-cellulite agents, antiperspirant agents, agents stimulating healing, coadjuvant healing agents, agents stimulating re-epithelialization, coadjuvant re-epithelialization agents, cytokine growth factors, calming agents, anti-inflammatory and/or analgesic agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, hair loss retardant agents, preservatives, perfumes, chelating agents, vegetable extracts, essential oils, marine extracts, agents obtained from a bio-fermentation process, mineral salts, cell extracts and sunscreens, organic or mineral photoprotective agents active against ultraviolet A and/or B rays or mixtures thereof.

16. A method of care of the skin, mucous membranes and/or hair, which comprises administering an effective amount of at least one peptide of general formula (I), its stereoisomers, mixtures thereof and/or its cosmetically or pharmaceutically acceptable salts, according to claim 1.

17. A method of treatment and/or care of the skin, mucous membranes and/or hair, which comprises administering an effective amount of at least one peptide of general formula (I):

$$R_1—W_n—X_m\text{-}AA_1\text{-}AA_2\text{-}AA_3\text{-}AA_4\text{-}Y_p—Z_q—R_2 \qquad (I),$$

its stereoisomers, mixtures thereof and/or its cosmetically or pharmaceutically acceptable salts,
wherein:
$AA_1$ is -His-;
$AA_2$ is selected from the group consisting of -His-, -Leu- and -Pro-;
$AA_3$ is -Leu-;
$AA_4$ is selected from the group consisting of -Arg- and -Asn-;
W, X, Y and Z are independently selected from amongst themselves from the group consisting of the codified amino acids and uncodified amino acids;
n, m, p and q are independently selected from amongst themselves and have a value between 0 and 1; n+m+p+q is less or equal to 2;
$R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group consisting of —$NR_3R_4$, —$OR_3$ and —$SR_3$, wherein $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl;

with the proviso that when $AA_2$ is -Leu-, $AA_4$ is -Asn- and Y is -Gln- then Z is not -Leu-;

and with the proviso that when $AA_2$ is -His-, $AA_4$ is -Arg- and Y or Z are -Tyr- then p+q is not 1;

in which said treatment and/or care:
(i) reduces or delays cell damage induced by UV radiation, thermal stress, oxidative stress, osmotic shock, inflammation, hypoxia, exposure to pollutants, lack of nourishment and lack of hydration,
(ii) reduces or delays the signs of aging and/or photoaging,
(iii) stimulates healing and/or re-epithelialization of wounds;
(iv) delays hair loss, or
(v) is a treatment of epidermolysis bullosa or alopecia.

\* \* \* \* \*